US011925626B2

(12) United States Patent
Scott et al.

(10) Patent No.: US 11,925,626 B2
(45) Date of Patent: *Mar. 12, 2024

(54) PHARMACEUTICAL FORMULATIONS CONTAINING RELACORILANT, A HETEROARYL-KETONE FUSED AZADECALIN COMPOUND

(71) Applicant: Corcept Therapeutics Incorporated, Menlo Park, CA (US)

(72) Inventors: Ian Scott, Dublin, CA (US); Travis Lemons, Palo Alto, CA (US); Yip-Fong Chia, Sunnyvale, CA (US)

(73) Assignee: Corcept Therapeutics Incorporated, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/950,902

(22) Filed: Sep. 22, 2022

(65) Prior Publication Data

US 2023/0032377 A1 Feb. 2, 2023

Related U.S. Application Data

(63) Continuation of application No. 16/719,644, filed on Dec. 18, 2019, now Pat. No. 11,464,764.

(60) Provisional application No. 62/781,983, filed on Dec. 19, 2018.

(51) Int. Cl.
| | | |
|---|---|---|
| *A61K 31/4375* | (2006.01) | |
| *A61K 9/00* | (2006.01) | |
| *A61K 9/48* | (2006.01) | |
| *A61K 31/437* | (2006.01) | |
| *A61K 47/10* | (2017.01) | |
| *A61K 47/14* | (2017.01) | |
| *A61K 47/26* | (2006.01) | |

(52) U.S. Cl.
CPC .......... *A61K 31/437* (2013.01); *A61K 9/0053* (2013.01); *A61K 9/4808* (2013.01); *A61K 9/4866* (2013.01); *A61K 47/10* (2013.01); *A61K 47/14* (2013.01); *A61K 47/26* (2013.01)

(58) Field of Classification Search
CPC ................................................. A61K 31/4375
See application file for complete search history.

(56) References Cited

U.S. PATENT DOCUMENTS

| | | | |
|---|---|---|---|
| 4,963,558 A | 10/1990 | Hotten et al. | |
| 5,696,127 A | 12/1997 | Jones et al. | |
| 6,166,013 A | 12/2000 | Coghlan et al. | |
| 6,583,180 B2 | 6/2003 | Link et al. | |
| 6,680,310 B2 | 1/2004 | Belanoff et al. | |
| 7,576,076 B2 | 8/2009 | Clark et al. | |
| 7,678,813 B2 | 3/2010 | Clark et al. | |
| 7,790,745 B2 | 9/2010 | Yang et al. | |
| 7,799,782 B2 | 9/2010 | Munson et al. | |
| 7,928,237 B2 | 4/2011 | Clark et al. | |
| 8,003,689 B2 | 8/2011 | Veverka | |
| 8,173,674 B2 | 5/2012 | Keil et al. | |
| 8,461,172 B2 | 6/2013 | Clark et al. | |
| 8,598,154 B2 | 12/2013 | Clark et al. | |
| 8,658,128 B2 | 2/2014 | Altschul et al. | |
| 8,685,973 B2 | 4/2014 | Clark et al. | |
| 8,710,035 B2 | 4/2014 | Pan et al. | |
| 8,859,774 B2 | 10/2014 | Hunt et al. | |
| 8,969,557 B2 | 3/2015 | Harriman et al. | |
| 9,107,926 B2 | 8/2015 | Belvin et al. | |
| 9,114,147 B2 | 8/2015 | Altschul et al. | |
| 9,149,485 B2 | 10/2015 | Pan et al. | |
| 9,273,047 B2 | 3/2016 | Hunt et al. | |
| 9,289,436 B2 | 3/2016 | Szmulewitz et al. | |
| 9,314,473 B2 | 4/2016 | Altschul et al. | |
| 9,320,747 B1 | 4/2016 | Altschul et al. | |
| 9,422,323 B2 | 8/2016 | Houpis et al. | |
| 9,623,032 B2 | 4/2017 | Pan et al. | |
| 9,707,223 B2 | 7/2017 | Hunt et al. | |
| 9,801,893 B2 | 10/2017 | Szmulewitz et al. | |

(Continued)

FOREIGN PATENT DOCUMENTS

| | | | |
|---|---|---|---|
| CL | 2014001241 A1 | 11/2014 | |
| CL | 2014003162 A1 | 2/2015 | |

(Continued)

OTHER PUBLICATIONS

Jannin, V., et al. "Polyoxylglycerides and glycerides: Effects of manufacturing parameters on API stability, excipient functionality and processing." International J of Pharmaceutics. (2014), vol. 466, pp. 109-121. (Year: 2014).*

"Capryol® 90—Propylene glycol monocaprylate type II." Accessed Nov. 14, 2021. First made available to public on May 28, 2017. Available from: <https://www.gattefosse.com/pharmaceuticals-products/capryol-90 > . (Year: 2017).*

"Preservatives and Antioxidants Database—Compounding Today." Accessed Nov. 15, 2021. First available to public on: Oct. 29, 2005. Available at: <CompoundingToday.com | Preservatives and Antioxidants Database >. (Year: 2005).*

(Continued)

*Primary Examiner* — John S Kenyon
(74) *Attorney, Agent, or Firm* — Kilpatrick Townsend & Stockton LLP

(57) ABSTRACT

Disclosed herein are novel formulations containing relacorilant ((R)-(1-(4-fluorophenyl)-6-(1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone) that are suitable for administration, including oral administration, to patients suffering from disorders amenable to treatment by glucocorticoid receptor modulators (GRMs). Single unit dosage forms comprise softgel capsules containing these formulations. Such softgel capsules may contain, e.g., relacorilant formulations containing 25 milligrams (mg), 50 mg, 100 mg, 200 mg, 300 mg, 400 mg, 500 mg, or other amounts of relacorilant. These novel formulations and single unit dosage forms may be used to treat diseases and disorders including Cushing's syndrome, Cushing's Disease, and other disorders.

21 Claims, 3 Drawing Sheets

(56) References Cited

U.S. PATENT DOCUMENTS

| | | |
|---|---|---|
| 9,829,495 B2 | 11/2017 | Moraitis |
| 9,943,505 B2 | 4/2018 | Hunt et al. |
| 9,956,216 B2 | 5/2018 | Hunt et al. |
| 10,047,082 B2 | 8/2018 | Hunt et al. |
| 10,117,852 B2 | 11/2018 | Hunt et al. |
| 10,213,414 B2 | 2/2019 | Hunt et al. |
| 10,413,540 B2 | 9/2019 | Hunt |
| 10,456,392 B2 | 10/2019 | Hunt et al. |
| 10,568,880 B2 | 2/2020 | Hunt |
| 10,898,478 B2 | 1/2021 | Hunt |
| 10,973,813 B2 | 4/2021 | Hunt et al. |
| 11,464,764 B2 | 10/2022 | Scott et al. |
| 2002/0115613 A1 | 8/2002 | Kumar |
| 2003/0064974 A1 | 4/2003 | Belanoff |
| 2004/0102422 A1 | 5/2004 | Gaston |
| 2004/0229855 A1 | 11/2004 | Belanoff |
| 2005/0085464 A1 | 4/2005 | Sapse et al. |
| 2005/0124533 A1 | 6/2005 | Schatzberg et al. |
| 2005/0245588 A1 | 11/2005 | Ali et al. |
| 2006/0063748 A1 | 3/2006 | Belanoff |
| 2007/0128627 A1 | 6/2007 | Simons, Jr. et al. |
| 2007/0203179 A1 | 8/2007 | Clark et al. |
| 2007/0281928 A1 | 12/2007 | Clark et al. |
| 2008/0070950 A1 | 3/2008 | Benjamin et al. |
| 2008/0287419 A1 | 11/2008 | Bruncko et al. |
| 2009/0156672 A1 | 6/2009 | Budunova et al. |
| 2010/0135956 A1 | 6/2010 | Gant et al. |
| 2010/0179115 A1 | 7/2010 | Belanoff |
| 2010/0292477 A1 | 11/2010 | Clark et al. |
| 2011/0166110 A1 | 7/2011 | Clark et al. |
| 2011/0166115 A1 | 7/2011 | Belanoff |
| 2011/0269728 A1 | 11/2011 | Pan et al. |
| 2012/0022121 A1 | 1/2012 | Dalton et al. |
| 2012/0201747 A1 | 8/2012 | Altschul et al. |
| 2012/0220565 A1 | 8/2012 | Clark et al. |
| 2013/0225633 A1 | 8/2013 | Hunt et al. |
| 2014/0005158 A1 | 1/2014 | Belanoff |
| 2014/0038926 A1 | 2/2014 | Hunt et al. |
| 2015/0080389 A1 | 3/2015 | Hunt et al. |
| 2015/0196640 A1 | 7/2015 | Cacase et al. |
| 2016/0215049 A1 | 7/2016 | Feldhaus et al. |
| 2017/0020860 A1 | 1/2017 | Hunt et al. |
| 2017/0273972 A1 | 9/2017 | Hunt et al. |
| 2018/0125856 A1 | 5/2018 | Moraitis et al. |
| 2018/0193313 A1 | 7/2018 | Hunt et al. |
| 2018/0280378 A1 | 10/2018 | Hunt |
| 2018/0325891 A1 | 11/2018 | Scott et al. |
| 2019/0076424 A1 | 3/2019 | Hunt |
| 2020/0197372 A1 | 6/2020 | Scott et al. |
| 2021/0169872 A1 | 6/2021 | Hunt et al. |

FOREIGN PATENT DOCUMENTS

| | | |
|---|---|---|
| CL | 56987 | 12/2018 |
| CN | 101027301 A | 8/2007 |
| CN | 104619328 A | 5/2015 |
| CN | 107530435 A | 1/2018 |
| CN | 104619328 B | 10/2018 |
| EP | 0145121 A2 | 6/1985 |
| EP | 0375210 A1 | 6/1990 |
| EP | 2854814 B1 | 1/2018 |
| EP | 3338781 B1 | 9/2019 |
| HK | 1208818 A | 3/2016 |
| HK | 1208818 B | 7/2018 |
| IL | 235868 | 4/2018 |
| IN | 10279/DELNP/2014 | 8/2016 |
| JP | 09505030 A | 5/1997 |
| JP | 2002506032 A | 2/2002 |
| JP | 2002544271 A | 12/2002 |
| JP | 2007528417 A | 10/2007 |
| JP | 2008520606 A | 6/2008 |
| JP | 2015517580 A1 | 6/2015 |
| JP | 6172871 B | 7/2017 |
| KR | 1020150021955 | 3/2015 |
| KR | 102062640 B1 | 12/2019 |
| MX | 365423 | 6/2019 |
| MY | 172739 A | 12/2019 |
| PE | 20542014 A1 | 1/2015 |
| PE | 9466 | 4/2019 |
| RU | 2009126745 A | 1/2011 |
| RU | 2014152625 A | 7/2016 |
| RU | 2639867 C2 | 12/2017 |
| WO | 9504734 A1 | 2/1995 |
| WO | 9945925 A1 | 9/1999 |
| WO | 0069846 A1 | 11/2000 |
| WO | 03015692 A2 | 2/2003 |
| WO | 03061651 A1 | 7/2003 |
| WO | 2005087769 A1 | 9/2005 |
| WO | 2009064738 A2 | 5/2009 |
| WO | 2011113015 A2 | 9/2011 |
| WO | 2011113015 A3 | 10/2011 |
| WO | 2012027702 A1 | 3/2012 |
| WO | 2013039916 A1 | 3/2013 |
| WO | 2013177559 A2 | 11/2013 |
| WO | 2013177559 A3 | 1/2014 |
| WO | 2015077530 A1 | 5/2015 |
| WO | 2016014365 A1 | 1/2016 |
| WO | 2016055533 A1 | 4/2016 |
| WO | 2016141365 A1 | 9/2016 |
| WO | 2017023694 A1 | 2/2017 |
| WO | 2017151613 A1 | 9/2017 |
| WO | WO-2017151613 A1 * | 9/2017 ........... A61K 31/437 |
| WO | 2020172501 A1 | 8/2020 |
| ZA | 201408182 B | 9/2017 |

OTHER PUBLICATIONS

"Chemical Processing", Available Online at: https://www.chemicalprocessing.com/, 2004, 8 pages.

"Mifeprex (Mifepristone) Tablets, 200mg For Oral Administration Only", Mifeprex (Mifepristone) Label, Rev 2, Jul. 19, 2005, pp. 1-20.

"Preservatives and Antioxidants Database", Available Online at: CompoundingToday.com I Preservatives and Antioxidants Database, Oct. 29, 2005, 3 pages.

"Propylene Glycol Monocaprylate Type II", Capryol® 90, Available Online at: https://www.gattefosse.com/pharmaceuticals-products/capryol-90, May 28, 2017, 3 pages.

"Study of Drug 1 (Enzalutamide) Plus Drug 2 (Relacorilant) for Patients With Prostate Cancer", ClinicalTrials.gov, Available Online at: www.clinicaltrials.gov/ct2/show/NCT03674814, Accessed from internet on Apr. 10, 2019, 9 pages.

"Study of Relacorilant in Combination with Nab-Paclitaxel for Patients with Recurrent Platinum-Resistant Ovarian, Fallopian Tube, or Primary Peritoneal Cancer", ClinicalTrials.gov, Available Online at: www.clinicaltrials.gov/ct2/show/NCT03776812, Accessed from Internet on Apr. 30, 2019, 11 pages.

"Study to Evaluate Cort125134 in Combination with Nab-Paclitaxel in Patients with Solid Tumors", ClinicalTrials.gov, Available Online at: www.clinicaltrials.gov/ct2/show/NCT02762981, Accessed from internet on Apr. 30, 2019, 7 pages.

U.S. Appl. No. 13/001,211 , "Final Office Action", dated Jun. 7, 2013, 12 pages.

U.S. Appl. No. 13/001,211 , "Non Final Office Action", dated Dec. 21, 2012, 14 pages.

U.S. Appl. No. 13/901,946 , "Non Final Office Action", dated Apr. 1, 2014, 8 Pages.

U.S. Appl. No. 13/901,946 , "Notice of Allowance", dated Jun. 26, 2014, 5 pages.

U.S. Appl. No. 14/487,347 , "Non-Final Office Action", dated Apr. 14, 2015, 5 pages.

U.S. Appl. No. 14/487,347 , "Notice of Allowance", dated Oct. 14, 2015, 7 pages.

U.S. Appl. No. 15/013,218 , "Non-Final Office Action", dated Dec. 2, 2016, 8 pages.

U.S. Appl. No. 15/013,218 , "Notice of Allowance", dated Mar. 17, 2017, 5 pages.

U.S. Appl. No. 15/621,013 , "Non-Final Office Action", dated Jan. 16, 2018, 7 pages.

(56) References Cited

OTHER PUBLICATIONS

U.S. Appl. No. 15/621,013 , "Notice of Allowance", dated Feb. 27, 2018, 5 pages.
U.S. Appl. No. 15/889,494 , "Final Office Action", dated Jun. 10, 2019, 7 pages.
U.S. Appl. No. 15/889,494 , "Non-Final Office Action", dated Jan. 2, 2019, 17 pages.
U.S. Appl. No. 15/889,494 , "Notice of Allowance", dated Jun. 28, 2019, 6 pages.
U.S. Appl. No. 16/570,839 , "Final Office Action", dated Sep. 30, 2020, 8 pages.
U.S. Appl. No. 16/570,839 , "Non-Final Office Action", dated Jun. 15, 2020, 12 pages.
U.S. Appl. No. 16/570,839 , "Notice of Allowance", dated Dec. 14, 2020, 7 pages.
U.S. Appl. No. 16/719,644 , "Non-Final Office Action", dated Nov. 18, 2021, 16 pages.
U.S. Appl. No. 16/719,644 , "Notice of Allowance", dated Jun. 3, 2022, 10 pages.
U.S. Appl. No. 16/719,644 , "Notice of Allowance", dated Jul. 28, 2022, 8 pages.
U.S. Appl. No. 16/742,198 , "Non-Final Office Action", dated May 1, 2020, 3 pages.
U.S. Appl. No. 16/742,198 , "Notice of Allowance", dated Aug. 21, 2020, 8 pages.
U.S. Appl. No. 16/742,198 , "Supplemental Notice of Allowability", dated Sep. 10, 2020, 2 pages.
Aherne et al., "Finding the Needle in the Haystack: Why Highthroughput Screening is Good for Your Health", Breast Cancer Research, vol. 4, No. 4, 2002, pp. 148-154.
Aisen et al., "A Randomized Controlled Trial of Prednisone in Alzheimer's Disease. Alzheimer's Disease Cooperative Study", Neurology, vol. 54, No. 3, Feb. 8, 2000, pp. 1-2.
Akiyama et al., "Inflammation and Alzheimer's Disease", Neurobiol Aging, vol. 21, No. 3, May-Jun. 2000, 66 pages.
Antonarakis et al., "Emerging Therapeutic Approaches in the Management of Metastatic Castration Resistant Prostate Cancer", Prostate Cancer and Prostatic Diseases, vol. 14, 2011, pp. 206-218.
Arrat et al., "ACTH (Acthar Gel) Reduces Toxic SOD1 Protein Linked to Amyotrophic Lateral Sclerosis in Transgenic Mice: A Novel Observation", PLoS One, vol. 10, No. 5, May 8, 2015, pp. 1-12.
Attard et al., "Translating Scientific Advancement into Clinical Benefit for Castration-Resistant Prostate Cancer Patients", Clinical Cancer Research, vol. 1, Issue 12, Jun. 2011, pp. 3867-3875.
AU2013266110 , "First Examiner Report", dated Sep. 19, 2016, 2 pages.
AU2013266110 , "Notice of Acceptance", dated Apr. 7, 2017, 3 pages.
Behl et al., "Protection Against Oxidative Stress-Induced Neuronal Cell Death—A Novel Role for RU486", European Journal of Neuroscience, vol. 9, No. 5, May 1997, pp. 912-920.
Belanoff et al., "Selective Glucocorticoid Receptor {Type II} Antagonists Prevent Weight Gain Caused by Olanzapine in Rats", European Journal of Pharmacology, vol. 655, No. 1-3, Mar. 25, 2011, pp. 117-120.
Belova et al., "Glucocorticoid Receptor Expression in Breast Cancer Associates with Older Patient Age", Breast Cancer Research and Treatment, vol. 116, No. 3, Aug. 2009, pp. 441-447.
Benagiano et al., "Selective Progesterone Receptor Modulators 3: Use in Oncology, Endocrinology and Psychiatry", Expert Opinion. Pharmacother, vol. 9, Issue 14, Oct. 2008, pp. 2487-2496.
Block et al., "Glucocorticoid Receptor Expression In 20 Solid Tumor Types Using Immunohistochemistry Assay", Cancer Management and Research, vol. 9, Mar. 6, 2017, pp. 65-72.
Bolton et al., "Cell- and Gene-Specific Regulation of Primary Target Genes by the Androgen Receptor", Genes Development, vol. 21, No. 16, Aug. 15, 2007, pp. 2005-2017.
Bolton et al., "The Effects of the Anti-Glucocorticoid RU 38486 on Steroid- Abstract Mediated Suppression of Experimental Allergic Encephalomyelitis (EAE) in the Lewis Rat", Life Sciences, vol. 45, No. 1, 1989, pp. 97-104.
BR112014028857-7 , "Office Action", dated Dec. 2, 2019, 4 pages.
Brusaferri et al., "Steroids for Multiple Sclerosis and Optic Neuritis: A Meta- Abstract Analysis of Randomized Controlled Clinical Trials", Journal of Neurology, vol. 247, No. 6, Jun. 2000, pp. 435-442.
CA2,872,260 , "Notice of Allowance", dated Sep. 30, 2020, 1 page.
CA2,872,260 , "Office Action", dated Apr. 14, 2020, 3 pages.
CA2,872,260 , "Office Action", dated Jun. 7, 2019, 3 pages.
CA2,872,260 , "Office Action", dated Nov. 30, 2018, 3 pages.
CA2,872,260 , "Office Action", dated Oct. 7, 2019, 3 pages.
Ca3, 121,193 , "Office Action", dated Sep. 14, 2022, 4 pages.
Caccamo et al., "Glucocorticoids Exacerbate Cognitive Deficits in TDP-25 Transgenic Mice Via a Glutathionemediated Mechanism: Implications for Aging, Stress and TDP-43 Proteinopathies", The Journal of Neuroscience, vol. 33, No. 3, Jan. 16, 2013, pp. 906-913.
Carri et al., "Neurodegeneration in Amyotrophic Lateral Sclerosis: The Role of Oxidative Stress and Altered Homeostasis of Metals", Brain Research Bulletin, vol. 61, Issue 4, Aug. 30, 2003, pp. 365-374.
Chan et al., "Prognostic Significance of Gleason Score 3+4 versus Gleason Score 4+3 Tumor at Radical Prostatectomy", Adult Urology, vol. 56, No. 5, Nov. 2000, pp. 823-827.
Check et al., "Evidence that Mifepristone, A Progesterone Receptor Antagonist, Can Cross the Blood Brain Barrier and Provide Palliative Benefits for Glioblastoma Multiforme Grade IV", Anticancer Research, vol. 34, No. 5, May 2014, pp. 2385-2388.
Check et al., "Mifepristone Causing Complete Remission of Rapidly Advancing Leukemia with Measurement of Progesterone-Induced Blocking Factor", Anticancer Research, vol. 34, No. 5, May 2014, pp. 2413-2416.
Chen et al., "Androgen and Glucocorticoid Receptor Heterodimer Formation: A Possible Mechanism for Mutual Inhibition of Transcriptional Activity", Journal of Biological Chemistry, vol. 272, No. 22, May 30, 1997, pp. 14087-14092.
Chen et al., "Mechanism of the Reversal Effect of Mifepristone on Drug Resistance of the Human Cervical Cancer Cell Line HELA/ MMC", Genetics and Molecular Research, vol. 13, No. 1, 2014, pp. 1288-1295.
Chi et al., "Castration-Resistant Prostate Cancer: From New Pathophysiology to New Treatment Targets", European Urology, vol. 56, Issue 4, Oct. 2009, pp. 594-605.
Cho et al., "Role of Activation function Domain-1, DNA Binding, and Coactivator GRIP1 in the Expression of Partial Agonist Activity of Glucocorticoid Receptor-Antagonist Complexes", Biochemistry, vol. 44, No. 9, Mar. 8, 2005, pp. 3547-3561.
CL2014-03173 , "Substantive Examination Report", dated Feb. 11, 2016, 11 pages.
CL2014-03173 , "Substantive Examination Report", dated Sep. 19, 2016, 6 pages.
Clark et al., "1H-Pyrazolo[3,4-g]Hexahydro-Isoquinolines as Selective Glucocorticoid Receptor Antagonists with High Functional Activity", Bioorganic & Medicinal Chemistry Letters, vol. 18, No. 4, Feb. 15, 2008, pp. 1312-1317.
Clark , "Glucocorticoid Receptor Antagonists", Current Topics in Medicinal Chemistry, vol. 8, No. 9, Jun. 1, 2008, pp. 813-838.
Cleutjens et al., "Both Androgen Receptor and Glucocorticoid Receptor Are Able to Induce Prostate-Specific Antigen Expression, but Differ in Their Growth-Stimulating Properties of LNCaP Cells", Endocrinology, vol. 138, Issue 12, Dec. 1, 1997, pp. 5293-5300.
CN201380039218.1 , "Notice of Decision To Grant", dated Aug. 29, 2018, 4 pages.
CN201380039218.1 , "Office Action", dated Nov. 30, 2016, 10 pages.
CN201380039218.1 , "Office Action", dated Jan. 6, 2016, 14 pages.
CN201380039218.1 , "Office Action", dated Dec. 12, 2017, 7 pages.
CN201380039218.1 , "Office Action", dated Jun. 16, 2017, 9 pages.
CN201980084873.6 , "Office Action", dated Jul. 8, 2022, 7 pages.
CO14-256677 , "Office Action", dated Jan. 4, 2016, 7 pages.

(56) References Cited

OTHER PUBLICATIONS

CO14-256677, "Substantive Examination Report", dated Oct. 7, 2015, 7 pages.

Colleoni et al., "Response to Primary Chemotherapy in Breast Cancer Patients with Tumors Not Expressing Estrogen and Progesterone Receptors", Annals of Oncology, vol. 11, No. 8, Aug. 1, 2000, pp. 1057-1059.

Cossu et al., "The Role of Mifepristone in Meningiomas Management: A Systematic Review of the Literature", BioMed Research International, vol. 2015, Jul. 2015, pp. 1-11.

Cummings et al., "Treatment Combinations for Alzheimer's Disease: Current and Future Pharmacotherapy Options", Journal of Alzheimer's Disease, vol. 67, Jan. 2019, pp. 779-794.

Damia et al., "Contemporary Pre-clinical Development of Anticancer Agents—What are the Optimal Preclinical Models", European Journal of Cancer, vol. 45, No. 16, Nov. 2009, pp. 2768-2781.

Davies et al., "Association of Glucocorticoid Receptors with Prostate Nuclear Sites for Androgen Receptors and with Androgen Response Elements", Journal of Molecular Endocrinology, vol. 5, Issue 2, Oct. 1990, pp. 117-127.

De Bono et al., "Abiraterone and Increased Survival in Metastatic Prostate Cancer", New England Journal of Medicine, vol. 364, No. 21, May 26, 2011, 19 pages.

Desmedt et al., "Strong Time Dependence of the 76-Gene Prognostic Signature for Node-Negative Breast Cancer Patients in the TRANSBIG Multicenter Independent Validation Series", Clinical Cancer Research, vol. 13, Issue 11, Jun. 2007, pp. 3207-3214.

Di Lorenzo et al., "Castration-Resistant Prostate Cancer", Drugs, vol. 70, Issue 8, May 2010, pp. 983-1000.

Dinkel et al., "Novel Glucocorticoid Effects on Acute Inflammation in the CNS", Journal of Neurochemistry, vol. 84, Feb. 2003, pp. 705-716.

Donovan et al., "Androgen Receptor Expression is Associated with Prostate Cancer-Specific Survival in Castrate Patients with Metastatic Disease", Bob Jones University International, vol. 105, No. 4, Feb. 2010, pp. 462-467.

EP09774351.2, "Extended European Search Report", dated May 7, 2012, 7 pages.

EP13751132.5, "Extended European Search Report", dated Mar. 21, 2016, 14 pages.

EP13751132.5, "Partial Supplementary European Search Report", dated Sep. 7, 2015, 6 pages.

EP13793417.0, "Decision to Grant", dated Jan. 5, 2018, 3 pages.

EP13793417.0, "Extended European Search Report", dated Jan. 4, 2016, 7 pages.

EP13793417.0, "Office Action", dated Oct. 11, 2016, 4 pages.

EP16183642.4, "Extended European Search Report", dated Dec. 1, 2016, 12 pages.

EP18154256.4, "Extended European Search Report", dated Mar. 26, 2018, 6 pages.

EP18154256.4, "Notice of Decision to Grant", dated Aug. 16, 2019, 3 pages.

EP18777520.0, "Extended European Search Report", dated Jul. 16, 2020, 9 pages.

EP19188885.8, "Extended European Search Report", dated Oct. 28, 2019, 6 pages.

EP19188885.8, "Notice of Decision to Grant", dated Feb. 18, 2021, 3 pages.

EP19898009.6, "Extended European Search Report", dated Sep. 8, 2022, 14 pages.

EP21154665.0, "Extended European Search Report", dated Apr. 23, 2021, 5 pages.

Evans et al., "CNS-Targeted Glucocorticoid Reduces Pathology in Mouse Model of Amyotrophic Lateral Sclerosis", Acta Neuropathologica Communications, vol. 2, No. 66, Jun. 13, 2014, pp. 1-13.

Fakih et al., "Glucocorticoids and Treatment of Prostate Cancer: A Preclinical and Clinical Review", Urology, vol. 60, Issue 4, Oct. 2002, pp. 553-561.

Fidler et al., "Disease Progression in a Mouse Model of Amyotrophic Lateral Sclerosis: The Influence of Chronic Stress and Corticosterone", The FASEB Journal, vol. 25, Dec. 2011, pp. 4369-4377.

Fiorentino et al., "Blood and Tissue Biomarkers in Prostate Cancer: State of the Art", Urologic Clinics of North America, vol. 37, Issue 1, Feb. 2010, pp. 1-14.

Flexner et al., "HIV Drug Development: The Next 25 Years", Nature Reviews, Drug Discovery, Dec. 2007, pp. 959-966.

Fradet, "PSA and Beyond: Biomarkers in Prostate Cancer Diagnosis and Prognosis", Current Opinion in Urology, vol. 19, Issue 3, May 2009, pp. 243-246.

Gaddy et al., "Mifepristone Induces Growth Arrest, Caspase Activation, and Apoptosis of Estrogen Receptor-Expressing, Antiestrogen-Resistant Breast Cancer Cells", Clinical Cancer Research, vol. 10, No. 15, Aug. 1, 2004, pp. 5215-5225.

Gargiulo-Monachelli et al., "Circulating Gonadal and Adrenal Steroids in Amyotrophic Lateral Sclerosis: Possible Markers of Susceptibility and Outcome", Hormone and Metabolic Research, vol. 46, Jun. 2014, pp. 433-439.

Genck, "Make the Most of Antisolvent Crystallization", Chemical Processing, Available Online at: https://www.chemicalprocessing.com/articles/2010/210/, Nov. 8, 2010, 8 pages.

Ghoumari et al., "Mifepristone (RU486) Protects Purkinje Cells from Cell Death in Organotypic Slice Cultures of Postnatal Rat and Mouse Cerebellum", Proceedings of the National Academy of Sciences, vol. 100, No. 13, Jun. 24, 2003, pp. 7953-7958.

Gonzalez et al., "Glucocorticoid Receptors and Actions in the Spinal Cord of the Wobbler Mouse, A Model for Neurodegenerative Diseases", Journal of Steroid Biochemistry and Molecular Biology, vol. 60, No. 3-4, Feb. 1997, pp. 205-213.

Grover et al., "The Initiation of Breast and Prostate Cancer", Carcinogenesis, vol. 23, No. 7, Jul. 1, 2002, pp. 1095-1102.

Gulliver, "Xenobiotics and the Glucocorticoid Receptor", Toxicology and Applied Pharmacology, vol. 319, Mar. 15, 2017, pp. 69-79.

Guo et al., "A Novel Androgen Receptor Splice Variant Is Up-Regulated During Prostate Cancer Progression and Promotes Androgen Depletion-Resistant Growth", Cancer Research, vol. 69, Issue 6, Mar. 15, 2009, pp. 2305-2313.

Han et al., "Biochemical (Prostate Specific Antigen) Recurrence Probability Following Radical Prostatectomy for Clinically Localized Prostate Cancer", The Journal of Urology, vol. 169, Issue 2, Feb. 2003, pp. 517-523.

He et al., "Discovery of a Highly Potent Glucocorticoid for Asthma Treatment", Cell Discovery, vol. 1, No. 15035, Dec. 15, 2015, 13 pages.

Hein et al., "Click Chemistry, A powerful Tool for Pharmaceutical Sciences", Pharmaceutical Research, vol. 25, No. 10, Oct. 2008, pp. 2216-2230.

Hemmi et al., "Dramatic Response of Dropped Head Sign to Treatment with Steroid in Parkinson's Disease: Report of Three Cases", Internal Medicine, vol. 50, Jan. 2011, pp. 757-761.

Henderson et al., "Estrogens as a Cause of Human Cancer: the Richard and Hinda Rosenthal Foundation Award Lecture", Cancer Research, vol. 48, No. 2, Jan. 15, 1988, pp. 246-253.

Ho et al., "A Complex Response Element in Intron 1 of the Androgen-Regulated 20-kDa Protein Gene Displays Cell Type-Dependent Androgen Receptor Specificity", Journal of Biological Chemistry, vol. 268, No. 36, Dec. 25, 1993, pp. 27226-27235.

Huang et al., "Reversal Effect of Mifepristone on Adriamycin Resistance in Human Breast Cancer Cell Line MCF-7/ADM in Vitro and in Vivo", Journal of Central South University, Medical Sciences, vol. 35, No. 6, Jun. 2010, pp. 576-583.

Hunt et al., "1H-Pyrazolo[3,4-g]Hexahydro-Isoquinolines as Potent GR Antagonists with Reduced hERG Inhibition and an Improved Pharmacokinetic Profile", Bioorganic & Medicinal Chemistry Letters, vol. 25, No. 24, Dec. 15, 2015, pp. 5720-5725.

Hunt et al., "Assessment of Safety, Tolerability, Pharmacokinetics, and Pharmacological Effect of Orally Administered CORT125134: An Adaptive, Double-Blind, Randomized, Placebo-Controlled Phase 1 Clinical Study", Clinical Pharmacology in Drug Development, vol. 7, No. 4, 2018, pp. 408-421.

(56) References Cited

OTHER PUBLICATIONS

Hunt et al., "Identification of the Clinical Candidate (R)-(1-(4-Fluorophenyl)-6-((1-Methyl-1H-Pyrazol-4-yl)Sulfonyl)-4,4a,5,6,7,8-Hexahydro-1H-Pyrazolo[3,4-g]Isoquinolin-4a-yl)(4-(Trifluoromethyl)Pyridin-2-yl)Methanone (CORT125134): A Selective Glucocorticoid Receptor", Journal of Medicinal Chemistry, vol. 60, No. 8, Apr. 27, 2017, pp. 3405-3421.
Hunt et al., "Identification of the Clinical Candidate (R)-(1-(4-Fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor", Journal of Medicinal Chemistry, vol. 60, No. 8, Apr. 27, 2017, pp. 3405-3421.
Hunt et al., "Preclinical Efficacy of the Selective GR antagonist, CORT125134", American Association for Cancer Research, 2017, 1 page.
IL235868, "Notice of Allowance", dated Oct. 23, 2017, 4 pages.
IL235868, "Office Action", dated Aug. 4, 2015, 2 pages.
IL235868, "Office Action", dated Jan. 23, 2017, 2 pages.
IL235868, "Office Action", dated Jun. 14, 2017, 2 pages.
IL235868, "Office Action", dated Jul. 25, 2016, 3 pages.
IN10279/DELNP/2014, "First Examination Report", dated Jul. 17, 2018, 5 pages.
IN202117031274, "First Examination Report", dated Dec. 29, 2021, 5 pages.
Jannin et al., "Polyoxylglycerides and Glycerides: Effects of Manufacturing Parameters on API Stability, Excipient Functionality and Processing", International Journal of Pharmaceutics, vol. 466, May 15, 2014, pp. 109-121.
Jemal et al., "Cancer Statistics", CA: A Cancer Journal for Clinicians, vol. 60, Issue 5, Sep.-Oct. 2010, pp. 277-300.
Johnson et al., "Relationships Between Drug Activity in NCI Preclinical in Vitro and in Vivo Models and Early Clinical Trials", British Journal of Cancer, vol. 84, No. 10, May 18, 2001, pp. 1424-1431.
JP2007-503030, "Office Action", dated Feb. 23, 2011, 8 pages.
JP2015-514233, "Notice of Allowance", Jun. 29, 2017, 3 pages.
JP2015-514233, "Office Action", Jan. 23, 2017, 4 pages.
JP2021-536303, "Office Action", Sep. 27, 2022, 6 pages.
Kach et al., "Glucocorticoid Receptor Signaling in Breast and Prostate Cancers: Emergence as a Therapeutic Target", Science Translational Medicine, vol. 7, No. 305, Sep. 16, 2015, 9 pages.
Kach et al., "Selective Glucocorticoid Receptor Modulators (SGRMs) Delay Castrate- Resistant Prostate Cancer Growth", Molecular Cancer Therapeutics, vol. 16, No. 8, Aug. 2017, pp. 1680-1692.
Kadmiel et al., "Glucocorticoid Receptor Signaling in Health and Disease", Trends in Pharmacological Sciences, vol. 34, No. 9, Sep. 2013, pp. 518-530.
Keen et al., "The Biology of Breast Carcinoma", Cancer, vol. 97, No. 3, Feb. 1, 2003, pp. 825-833.
Kim et al., "Current Treatment Strategies for Castration-Resistant Prostate Cancer", Korean Journal of Urology, vol. 52, No. 3, Mar. 2011, pp. 157-165.
Klein et al., "Analyzing Survival Curves at a Fixed Point in Time", Statistics in Medicine, vol. 26, No. 24, Oct. 30, 2007, pp. 4505-4519.
Klijn et al., "Antiprogestins a New Form of Endocrine Therapy for Human Breast Cancer", Cancer Research, vol. 49, No. 11, Jun. 1, 1989, pp. 2851-2856.
Kondo et al., "A Case of Ectopic Adrenocorticotropic Hormone-Producing Pancreatic Neuroendocrine Tumor with Multiple Liver Metastases", Endocrine Journal, vol. 57, No. 3, Apr. 2010, pp. 229-236.
Koochekpour, "Androgen Receptor Signaling and Mutations in Prostate Cancer", Asian Journal of Andrology, vol. 12, Issue 5, Sep. 2010, pp. 639-657.
KR10-2014-7036405, "Notice of Decision to Grant", dated Nov. 26, 2019, 5 pages.
KR10-2014-7036405, "Office Action", dated Aug. 1, 2019, 5 pages.

Kriaucionis et al., "The Nuclear DNA Base 5-Hydroxymethylcytosine is Present in Brain and Enriched in Purkinje Neurons", Science, vol. 324, No. 5929, May 15, 2009, 5 pages.
Lante et al., "Subchronic Glucocorticoid Receptor Inhibition Rescues Early Episodic Memory and Synaptic Plasticity Deficits in a Mouse Model of Alzheimer's Disease", Neuropsychopharmacology, vol. 40, No. 7, Jun. 2015, pp. 1772-1781.
Li et al., "High Level of Androgen Receptor is Associated with Aggressive Clinicopathologic Features and Decreased Biochemical Recurrence-Free Survival in Prostate: Cancer Patients Treated with Radical Prostatectomy", The American Journal of Surgical Pathology, vol. 28, No. 7, Jul. 2004, pp. 928-934.
Li et al., "Systemic Overexpression of the 11β-HSD1 Promotes Endoplasmic Reticulum Stress in Multiple Tissues and the Development of Metabolic Syndrome in Mice", Molecular Medicine Reports, vol. 16, No. 5, Nov. 2017, pp. 7738-7744.
Loi et al., "Definition of Clinically Distinct Molecular Subtypes in Estrogen Receptor-Positive Breast Carcinomas Through Genomic Grade", Journal of Clinical Oncology, vol. 25, No. 10, Apr. 1, 2007, pp. 1239-1246.
Loi et al., "Predicting Prognosis Using Molecular Profiling in Estrogen Receptor-Positive Breast Cancer Treated With Tamoxifen", BMC Genomics, vol. 9, No. 239, May 22, 2008, pp. 1-12.
Lotan et al., "Up-Regulation of MKK4, MKK6 and MKK7 During Prostate Cancer Progression: An Important Role for SAPK Signalling in Prostatic Neoplasia", The Journal of Pathology, vol. 212, Issue 4, Aug. 2007, pp. 386-394.
Lucci et al., "Modification of Ceramide Metabolism Increases Cancer Cell Sensitivity to Cytotoxics", International Journal of Oncology, vol. 15, No. 3, Sep. 1999, pp. 541-546.
Ma et al., "IL-21 Activates Both Innate and Adaptive Immunity to Generate Potent Antitumor Responses that Require Perforin but Are Independent of IFN-Gamma", Journal of Immunology, vol. 171, No. 2, Jul. 15, 2003, pp. 608-615.
Macpherson et al., "Glucocorticoids Worsen Excitotoxin-Induced Expression of Pro-Infammatory Cytokines in Hippocarnpal Cultures", Experimental Neurology, vol. 194, No. 2, Aug. 2005, pp. 376-383.
Makarov et al., "Updated Nomogram to Predict Pathologic Stage of Prostate Cancer Given Prostate-Specific Antigen Level, Clinical Stage, and Biopsy Gleason Score (Partin Tables) Based on Cases from 2000 to 2005", Urology, vol. 69, Issue 6, Jun. 2007, pp. 1095-1101.
Melhem et al., "Administration of Glucocorticoids to Ovarian Cancer Patients is Associated with Expression of the Anti-apoptotic Genes SGK1 and MKP1/DUSP1 in Ovarian Tissues", Clinical Cancer Research, vol. 15, No. 9, May 1, 2009, pp. 3196-3204.
Meyer et al., "The Selective Glucocorticoid Receptor Modulator Cort 113176 Reduces Neurodegeneration and Neuroinflammation in Wobbler Mice Spinal Cord", Neuroscience, vol. 384, 2018, pp. 384-396.
Meyer et al., "The Selective Glucocorticoid Receptor Modulator CORT108297 Restores Faulty Hippocampal Parameters in Wobbler and Corticosterone-Treated Mice", The Journal of Steroid Biochemistry and Molecular Biology, vol. 143, Sep. 2014, pp. 40-48.
Mikosz et al., "Glucocorticoid Receptor-Mediated Protection from Apoptosis is Associated with Induction of the Serine/Threonine Survival Kinase Gene, sgk-1", The Journal of Biological Chemistry, vol. 276, No. 20, Feb. 13, 2001, pp. 16649-16654.
Miljkovic et al., "Methylprednisolone Inhibits IFN-Y and IL-17 Expression and Production by Cells Infiltrating Central Nervous System in Experimental Autoimmune Encephalomyelitis", Journal of Neuroinflammation, vol. 6, No. 37, 2009, pp. 1-10.
Minn et al., "Genes that Mediate Breast Cancer Metastasis to Lung", Nature, vol. 436, No. 7050, Jul. 28, 2005, pp. 518-524.
Mohler et al., "Androgen and Glucocorticoid Receptors in the Stroma and Epithelium of Prostatic Hyperplasia and Carcinoma", Clinical Cancer Research, vol. 2, Issue 5, May 1996, pp. 889-895.
Moller et al., "Impact of New Technologies for Cellular Screening along the Drug Value Chain", Drug Discovery Today, vol. 14, No. 9-10, May 2010, pp. 384-390.

(56) References Cited

OTHER PUBLICATIONS

Moran et al., "The Glucocorticoid Receptor Mediates a Survival Signal in Human Mammary Epithelial Cells", Cancer Research, vol. 60, No. 4, Feb. 15, 2000, pp. 867-872.
Moses et al., "The Growing Applications of Click Chemistry", Chemical Society Reviews, vol. 36, No. 8, May 2007, pp. 1249-1262.
Mottet et al., "EAU Guidelines on Prostate Cancer. Part II: Treatment of Advanced, Relapsing, and Castration- Resistant Prostate Cancer", European Urology, vol. 59, Jan. 2011, pp. 572-583.
Munhoz et al., "Chronic Unpredictable Stress Exacerbates Lipopolysaccharide-Induced Activation of Nuclear Factor-kappaB in the Frontal Cortex and Hippocampus Via Glucocorticoid Secretion", The Journal of Neuroscience, vol. 26, No. 14, Apr. 2006, pp. 3813-3820.
Munster et al., "A Phase 1/2 Study of Relacorilant + Nab-Paclitaxel (Nabpac) in Patients (Pts) with Solid Tumors: The Dose-Finding Phase", Journal of Clinical Oncology, vol. 36, No. 15, May 20, 2018, 4 pages.
Munster et al., "A Phase 1/2 Study of Relacorilant + Paclitaxel in Patients with Solid Tumors: The Dose-Finding Phase", American Association for Cancer Research, 2018, 1 page.
MX/A/2014/014239, "Notice of Decision to Grant", dated Apr. 23, 2019, 2 pages.
MX/A/2014/014239, "Office Action", dated Apr. 15, 2015, 2 pages.
MX/A/2014/014239, "Office Action", dated Jan. 24, 2019, 3 pages.
MX/A/2014/014239, "Office Action", dated Oct. 30, 2018, 3 pages.
MYPI2014003289, "Substantive Examination Adverse Report", dated Mar. 30, 2018, 2 pages.
Niemeier et al., "Androgen Receptor in Breast Cancer: Expression in Estrogen Receptor-Positive Tumors and in Estrogen Receptor-Negative Tumors with Apocrine Differentiation", Modern Pathology, vol. 23, No. 2, 2010, pp. 205-212.
Norman et al., "Functional Glucocorticoid Receptor Modulates Pancreatic Carcinoma Growth through an Autocrine Loop", Journal of Surgical Research., vol. 57, No. 1, Jul. 1994, pp. 33-38.
Novotny et al., "Cancer Therapy: New Targets for Chemotherapy", Hematology, vol. 8, No. 3, Jun. 2003, pp. 129-137.
Ocana et al., "Preclinical Development of Molecular-Targeted Agents for Cancer", Nature Reviews Clinical Oncology Review, vol. 8, No. 4, Apr. 2011, pp. 200-209.
Ohlmann et al., "Novel Options for the Treatment of Castration-Resistant Prostate Cancer", World Journal of Urology, vol. 30, No. 4, Aug. 2012, pp. 495-503.
Orayj et al., "Patterns and Determinants of Prescribing for Parkinson's Disease: A Systematic Literature Review", Parkinson's Disease, Review Article ID 9237181, vol. 2019, Nov. 2019, pp. 1-40.
Pan et al., "Activation of the Glucocorticoid Receptor is Associated with Poor Prognosis in Estrogen Receptor- Negative Breast Cancer", Cancer Research, vol. 71, No. 20, Oct. 15, 2011, 21 pages.
Pan et al., "Identification of Glucocorticoid Receptor (GR) Signatures in Primary Human Breast Cancer: Association with Relapse-Free Survival Time", Poster Presented by S.D. Conzen as a Short Talk, presented at Nuclear Receptors: Signaling, Gene Regulation and Cancer, Keystone Symposia on Molecular and Cellular Biology, Keystone Resort, Keystone, Colorado, Mar. 25, 2010, 1 page.
Pang et al., "Dexamethasone Decreases Xenograft Response to Paclitaxel Through Inhibition of Tumor Cell Apoptosis", Cancer Biology & Therapy, vol. 5, No. 8, Aug. 2006, pp. 933-940.
Panigrahi et al., "Gelucire: A Versatile Polymer for Modified Release Drug Delivery System", Future Journal of Pharmaceutical Sciences, vol. 4, No. 1, Apr. 2018, pp. 102-108.
Patacchioli et al., "Adrenal Dysregulation in Amyotrophic Lateral Sclerosis", Journal of Endocrinological Investigation, vol. 26, No. 12, Dec. 2003, pp. 1-6.
PCT/US13/27720, "International Search Report and Written Opinion", dated Jun. 17, 2013, 9 pages.
PCT/US2005/008049, "International Search Report and Written Opinion", dated Jun. 15, 2005, 8 pages.
PCT/US2009/49273, "International Search Report and Written Opinion", dated Aug. 14, 2009, 7 pages.
PCT/US2010/034382, "International Search Report and Written Opinion", dated Jul. 9, 2010, 7 pages.
PCT/US2011/049408, "International Search Report and Written Opinion", dated Jan. 30, 2012, 10 pages.
PCT/US2013/027150, "International Preliminary Report on Patentability", dated Sep. 4, 2014, 7 pages.
PCT/US2013/027150, "International Search Report and Written Opinion", dated Apr. 29, 2013, 9 pages.
PCT/US2013/027720, "International Search Report and Written Opinion", dated Jun. 17, 2013, 8 pages.
PCT/US2013/042732, "International Preliminary Report on Patentability", dated Dec. 4, 2014, 6 pages.
PCT/US2013/042732, "International Search Report and Written Opinion", dated Nov. 13, 2013, 8 pages.
PCT/US2018/025547, "International Search Report and Written Opinion", dated Aug. 9, 2018, 13 pages.
PCT/US2019/067108, "International Preliminary Report on Patentability", dated Jul. 1, 2021, 7 pages.
PCT/US2019/067108, "International Search Report and Written Opinion", dated Apr. 21, 2020, 15 pages.
PE2054-2014, "Notice of Grant", dated Apr. 24, 2019, 10 pages.
PE2054-2014, "Office Action", dated Jan. 10, 2019, 10 pages.
Peeters et al., "Differential Effects of the New Glucocorticoid Receptor Antagonist ORG 34517 and RU486 (Mifepristone) on Glucocorticoid Receptor Nuclear Translocation in the AtT20 Cell Line", Annals of the New York Academy of Sciences, vol. 1148, No. 1, Dec. 2008, pp. 536-541.
Perini et al., "Effects of Carbamazepine on Pituitary-Adrenal Function in Healthy Volunteers", The Journal of Clinical Endocrinology and Metabolism, vol. 74, No. 2, Feb. 1, 1992, pp. 406-412.
Petrov et al., "ALS Clinical Trials Review: 20 Years of Failure. Are we Any Closer to Registering a New Treatment?", Frontiers in Aging Neuroscience, vol. 9, No. 68, Mar. 2017, pp. 1-11.
Petrylak et al., "Evaluation of Prostate-Specific Antigen Declines for Surrogacy in Patients Treated on SWOG 99-16", Journal of the National Cancer Institute, vol. 98, Issue 8, Apr. 19, 2006, pp. 516-521.
PH1-2014-502584, "Notice of Allowance", dated Oct. 26, 2015, 1 page.
PH1-2014-502584, "Substantive Examination Report", dated Jul. 27, 2015, 1 page.
Pike et al., "Estrogens, Progestogens, Normal Breast Cell Proliferation, and Breast Cancer Risk", Epidemiologic Reviews, vol. 15, No. 1, Jan. 1, 1993, pp. 17-30.
Pomara et al., "Mifepristone (RU 486) for Alzheimer's Disease", Neurology, vol. 58, May 2002, pp. 1436-1437.
Pound et al., "Natural History of Progression after PSA Elevation Following Radical Prostatectomy", JAMA, vol. 281, No. 17, May 5, 1999, pp. 1591-1597.
Rakotomamonjy et al., "Brain-Derived Neurotrophic Factor is Required for the Neuroprotective Effect of Mifepristone on Immature Purkinje Cells in Cerebellar Slice Culture", International Journal of Molecular Sciences., vol. 20, No. 2, Jan. 12, 2019, pp. 1-9.
Rauhala et al., "Dual-Specificity Phosphatase 1 and Serum/Glucocorticoid-Regulated Kinase are Downregulated in Prostate Cancer", International Journal of Cancer, vol. 117, Issue 5, Dec. 10, 2005, pp. 738-745.
Ring et al., "Mechanisms of Tamoxifen Resistance", Endocrine-Related Cancer, vol. 11, No. 4, Dec. 2004, pp. 643-658.
Robinson et al., "Octahydrophenanthrene-2,7-diol Analogues as Dissociated Glucocorticoid Receptor Agonists: Discovery and Lead Exploration", Journal of Medicinal Chemistry, vol. 52, No. 6, 2009, pp. 1731-1743.
Roozendaal et al., "The Cortisol Awakening Response in Amyotrophic Lateral Sclerosis is Blunted and Correlates with Clinical Status and Depressive Mood", Psychoneuroendocrinology, vol. 37, Jan. 2012, pp. 20-26.
Rosner et al., "Higher Tumor to Benign Ratio of the Androgen Receptor mRNA Expression Associates with Prostate Cancer Progression after Radical Prostatectomy", Urology, vol. 70, Issue 6, Dec. 2007, pp. 1225-1229.
RU2014152625, "Notice of Decision to Grant", dated Sep. 1, 2017, 28 pages.

(56) References Cited

OTHER PUBLICATIONS

RU2014152625, "Office Action", dated Apr. 17, 2017, 16 pages.
RU2021120817, "Notice of Decision to Grant", dated May 19, 2022, 11 pages.
Sahoo et al., "Coordinate Expression of the PI3-Kinase Downstream Effectors Serum and Glucocorticoid-Induced Kinase (SGK-1) and Akt-1 in Human Breast Cancer", European Journal of Cancer, vol. 41, No. 17, Nov. 2005, pp. 2754-2759.
Sahu et al., "FoxA1 Specifies Unique Androgen and Glucocorticoid Receptor Binding Events in Prostate Cancer Cells", Cancer Research, vol. 73, Issue 5, Mar. 2013, pp. 1570-1580.
Schenone et al., "Target Identification and Mechanism of Action in Chemical Biology and Drug Discovery", Nature Chemical Biology, vol. 9, No. 4, 2013, pp. 232-240.
Scher et al., "Antitumour Activity of Mdv3100 in Castration-Resistant Prostate Cancer: A Phase 1-2 Study", Lancet, vol. 375, No. 9724, Apr. 24, 2010, pp. 1437-1446.
Scher et al., "Biology of Progressive, Castration-Resistant Prostate Cancer: Directed Therapies Targeting the Androgen-Receptor Signaling Axis", Journal of Clinical Oncology, vol. 23, No. 32, Nov. 10, 2005, pp. 8253-8261.
Scher et al., "End Points and Outcomes in Castration-Resistant Prostate Cancer: From Clinical Trials to Clinical Practice", Journal of Clinical Oncology, vol. 29, No. 27, Sep. 20, 2011, pp. 3695-3704.
Schlossmacher et al., "Glucocorticoid Receptor-Mediated Apoptosis: Mechanisms of Resistance In Cancer Cells", Journal of Endocrinology, vol. 211, No. 1, Oct. 2011, pp. 17-25.
Segovia-Mendoza et al., "Antihormonal Agents as a Strategy to Improve the Effect of Chemo-Radiation in Cervical Cancer: In Vitro and in Vivo Study", BMC Cancer, vol. 15, No. 21, 2015, pp. 1-11.
Seruga et al., "Drug Resistance in Metastatic Castration-Resistant Prostate Cancer", Nature Reviews Clinical Oncology, vol. 8, No. 1, Jan. 2011, pp. 12-23.
SG11201407682T, "Notice of Decision to Grant", dated Feb. 15, 2017, 4 pages.
SG11202105770Y, "Written Opinion", dated Jul. 17, 2022, 8 pages.
Shanmugam et al., "Serum/Glucocorticoid-Induced Protein Kinase-1 Facilitates Androgen Receptor-Dependent Cell Survival", Cell Death Differ, vol. 14, No. 12, Oct. 12, 2007, pp. 2085-2094.
Sharma et al., "Cell Line-Based Platforms to Evaluate the Therapeutic Efficacy of Candidate Anticancer Agents", Nature Reviews Cancer, vol. 10, No. 4, Apr. 2010, pp. 241-253.
Sherk et al., "Development of a Small Molecule Serum and Glucocorticoid-Regulated Kinase 1 Antagonist and its Evaluation as a Prostate Cancer Therapeutic", Cancer Research, vol. 68, Issue 18, Sep. 2008, 20 pages.
Sims et al., "The Removal of Multiplicative, Systematic Bias Allows Integration of Breast Cancer Gene Expression Datasets - Improving Meta-Analysis and Prediction of Prognosis", BMC Medical Genomics, vol. 1, No. 42, Sep. 21, 2008, pp. 1-14.
Smith et al., "Expression of Glucocorticoid and Progesterone Nuclear Receptor Genes in Archival Breast Cancer Tissue", Breast Cancer Research, vol. 5, No. 1, 2003, pp. R9-R12.
Smith et al., "Progesterone, Glucocorticoid, but Not Estrogen Receptor mRNA is Altered in Breast Cancer Stroma", Cancer Letters, vol. 255, No. 1, Sep. 18, 2007, pp. 77-84.
Song et al., "Dihydrotestosterone Enhances Castration-Resistant Prostate Cancer Cell Proliferation through STAT5 Activation via Glucocorticoid Receptor Pathway", The Prostate, vol. 74, Issue 12, Sep. 2014, pp. 1240-1248.
Sorlie et al., "Gene Expression Patterns of Breast Carcinomas Distinguish Tumor Subclasses with Clinical Implications", Proceedings of the National Academy of Sciences of the United States of America, vol. 98, No. 19, Sep. 11, 2001, pp. 10869-10874.
Sotiriou et al., "Gene Expression Profiling in Breast Cancer: Understanding the Molecular Basis of Histologic Grade to Improve Prognosis", Journal of the National Cancer Institute, vol. 98, No. 4, Feb. 15, 2006, pp. 262-272.

Spataro et al., "Plasma Cortisol Level in Amyotrophic Lateral Sclerosis", Journal of the Neurological Sciences, vol. 358, Nov. 2015, pp. 282-286.
Srinivas et al., "Phase II Study Evaluating Oral Triamcinolone in Patients with Androgen-Independent Prostate Cancer", Adult Urology, vol. 67, No. 5, May 1, 2006, pp. 1001-1006.
Srinivas et al., "Proteomics for Cancer Biomarker Discovery", Clinical Chemistry, vol. 48, Issue 8, Aug. 2002, pp. 1160-1169.
Stephenson et al., "Preoperative Nomogram Predicting the 10-Year Probability of Prostate Cancer Recurrence After Radical Prostatectomy", Journal of the National Cancer Institute, vol. 98, No. 10, May 17, 2006, 7 pages.
Sterbis et al., "Higher Expression of the Androgen-Regulated Gene PSA-HK3 mRNA in Prostate Cancer Tissues Predicts Biochemical Recurrence-Free Survival", Clinical Cancer Research, vol. 14, Issue 3, Feb. 2008, pp. 758-763.
Stringer-Reasor et al., "Glucocorticoid Receptor Activation Inhibits Chemotherapy-Induced Cell Death in High-Grade Serous Ovarian Carcinoma", Gynecologic Oncology, vol. 138, No. 3, 2015, pp. 656-662.
Sui et al., "Estrogen Receptor a Mediates Breast Cancer Cell Resistance to Paclitaxel Through Inhibition of Apoptotic Cell Death", Cancer Research, vol. 67, No. 11, Jun. 1, 2007, pp. 5337-5344.
Sun et al., "Castration Resistance in Human Prostate Cancer is Conferred by a Frequently Occurring Androgen Receptor Splice Variant", Journal of Clinical Investigation, vol. 120, Issue 8, Aug. 2, 2010, pp. 2715-2730.
Sundahl et al., "Selective Glucocorticoid Receptor-Activating Adjuvant Therapy in Cancer Treatments", Oncoscience, vol. 3, No. 7-8, Jul. 2016, pp. 188-202.
Szmulewitz et al., "Serum/Glucocorticoid-Regulated Kinase 1 Expression in Primary Human Prostate Cancers", Prostate, vol. 72, Issue 2, Feb. 1, 2018=2, pp. 157-164.
Tannock et al., "Docetaxel Plus Prednisone or Mitoxantrone Plus Prednisone for Advanced Prostate Cancer", The New England Journal of Medicine, vol. 351, No. 15, Oct. 7, 2004, pp. 1502-1512.
Taplin et al., "A Phase II Study of Mifepristone (Ru-486) in Castration-Resistant Prostate Cancer, with a Correlative Assessment of Androgen-Related Hormones", BJU International, vol. 101, Issue 9, May 1, 2008, pp. 1084-1089.
Tessier et al., "Serum and Glucocorticoid-Regulated Protein Kinases: Variations on a Theme", Journal of Cellular Biochemistry, vol. 98, No. 6, Aug. 15, 2006, pp. 1391-1407.
Tokuda et al., "Prednisolone (30-60 Mg/Day) for Diseases Other than AD Decreases Amyloid B-peptides in CSF", Neurology, vol. 58, No. 9, May 14, 2002, 1 page.
Touat et al., "Successful Treatment of Multiple Intracranial Meningiomas with the Antiprogesterone Receptor Agent Mifepristone (RU486)", Acta Neurochirurgica, vol. 156, No. 10, Oct. 2014, pp. 1831-1835.
Twiddy et al., "Cholesterol as a Potential Target for Castration-Resistant Prostate Cancer", Pharmaceutical Research, vol. 28, Issue 3, Mar. 2011, pp. 423-437.
Venkatesh et al., "Role of the Development Scientist in Compound Lead Selection and Optimization", Journal of Pharmaceutical Sciences, vol. 89, No. 2, Feb. 2000, pp. 145-154.
Wang et al., "Gene-Expression Profiles to Predict Distant Metastasis of Lymph-Node-Negative Primary Breast Cancer", The Lancet, vol. 365, No. 9460, Feb. 19-25, 2005, pp. 671-679.
Ward et al., "Rising Prostate-Specific Antigen after Primary Prostate Cancer Therapy", Nature Clinical Practice Urology, vol. 2, No. 4, Apr. 1, 2005, pp. 174-182.
West et al., "Abstract PD3-02: Second-Generation Selective Glucocorticoid Receptor Modulators in Triple-Negative Breast Cancer", Cancer Research, Thirty-Eighth Annual CTRC-AACR, vol. 76, No. 4, Feb. 2016, pp. 1-4.
Wright et al., "Differences in Prostate Cancer Outcomes Between Cases With Gleason 4+3 and Gleason 3+4 Tumors in a Population Based Cohort", The Journal of Urology, vol. 182, Issue 6, Dec. 2009, pp. 2702-2707.
Wu et al., "Glucocorticoid Receptor Activation Signals Through Forkhead Transcription Factor 3a in Breast Cancer Cells", Molecular Endocrinology, vol. 20, No. 10, Oct. 1, 2006, pp. 2304-2314.

(56) References Cited

OTHER PUBLICATIONS

Wu et al., "Microarray Analysis Reveals Glucocorticoid-Regulated Survival Genes that are Associated with Inhibition of Apoptosis in Breast Epithelial Cells", Cancer Research, vol. 64, No. 5, Mar. 1, 2004, pp. 1757-1764.

Wu et al., "Prevalent Expression of the Immunostimulatory MHC Class I Chain-Related Molecule Is Counteracted by Shedding in Prostate Cancer", Journal of Clinical Investigation, vol. 114, Issue 4, Aug. 16, 2004, pp. 560-568.

Yemelyanov et al., "Differential Targeting of Androgen and Glucocorticoid Receptors Induces ER Stress and Apoptosis in Prostate Cancer Cells", Cell Cycle, vol. 11, Issue 2, Jan. 15, 2012, pp. 395-406.

Yemelyanov et al., "Tumor Suppressor Activity of Glucocorticoid Receptor in the Prostate", Oncogene, vol. 26, No. 13, Mar. 22, 2007, pp. 1885-1896.

Yu et al., "Systems Pharmacology of Mifepristone (RU486) Reveals its 47 Hub Targets and Network: Comprehensive Analysis and Pharmacological Focus on FAK-Src-Paxillin complex", Scientific Reports, vol. 5, No. 7830, 2015, pp. 1-10.

Zegarra-Moro et al., "Disruption of Androgen Receptor Function Inhibits Proliferation of Androgen-refractory Prostate Cancer Cells", Cancer Research, vol. 62, Issue 4, Feb. 2002, pp. 1008-1013.

Zhang et al., "Corticosteroid Co-Treatment Induces Resistance to Chemotherapy in Surgical Resections, Xenografts and Established Cell Lines of Pancreatic Cancer", BMC Cancer, vol. 6, No. 61, Mar. 15, 2006, pp. 1-14.

Zou et al., "Androgen-Induced Coactivator ANCCA Mediates Specific Androgen Receptor Signaling in Prostate Cancer", Cancer Res., vol. 69, Issue 8, Apr. 2009, pp. 3339-3346.

\* cited by examiner

PHARMACEUTICAL FORMULATIONS CONTAINING RELACORILANT, A HETEROARYL-KETONE FUSED AZADECALIN COMPOUND

CROSS-REFERENCE TO RELATED APPLICATION

This application is a continuation of U.S. patent application Ser. No. 16/719,644 filed Dec. 18, 2019, which claims priority to, and the benefit of, U.S. Patent Application No. 62/781,983, filed Dec. 19, 2018, the entire contents of which are hereby incorporated by reference in their entirety.

BACKGROUND

Many heteroaryl-ketone fused azadecalin compounds bind to glucocorticoid receptors (GRs) and may thereby have therapeutic activity. Such compounds and their activities are disclosed, for example, in U.S. Pat. Nos. 8,859,774; 9,273,047; 9,707,223; 9,943,505; 9,956,216; and others. Pharmaceutical formulations containing heteroaryl-ketone fused azadecalin compounds may be used for administration of those compounds to humans or animals for therapeutic purposes.

GRs play an important role in normal physiology, and the disruption or alteration of GR function is implicated in many diseases and disorders. The most important GR ligand in humans is cortisol. Cortisol binding to GR activates GR. Compounds which bind GRs and which affect GR activity may be termed glucocorticoid receptor modulators (GRMs). GRMs which reduce GR activity, e.g. by interfering with or competing for ligand binding to GR, are termed GR antagonists (GRAs). Diseases and disorders of abnormal GR activation include Cushing's syndrome (typically caused by excess cortisol), Addison's disease (typically caused by inadequate levels of cortisol), and others. Therapeutic uses for GRM compounds, whether as single agents or in combination with other agents, include treatments for endocrine disorders including Cushing's syndrome and Cushing's disease, cancer, immune system disorders, cardiovascular disorders including hypertension, diabetes, hyperglycemia, liver diseases, bone diseases, obesity, antipsychotic-induced weight gain, psychiatric disorders, addictive behaviors and disorders, and other diseases and disorders.

However, many GRM compounds are difficult to formulate in compositions suitable for administration to subjects in need of the compounds. Many such compounds are only sparingly soluble in water, may be incompatible with other ingredients typically used in pharmaceutical compositions, or may have other properties which make it difficult to prepare therapeutic formulations. Many GRM compounds are unstable, degrading over time, or with exposure to light or heat. Such characteristics of one heteroaryl-ketone fused azadecalin compound may differ from those of another heteroaryl-ketone fused azadecalin compound, so that a formulation suitable for one heteroaryl-ketone fused azadecalin compound may not be suitable for a different heteroaryl-ketone fused azadecalin compound.

For example, many heteroaryl-ketone fused azadecalin compounds are poorly soluble in water, and may have poor bioavailability in some formulations. Poor solubility or bioavailability necessitates the administration of large volumes of solution, large pills or tablets, or large numbers of pills or tablets in order to provide sufficient active compound for effective treatments. In addition, some heteroaryl-ketone fused azadecalin compounds, and formulations containing these compounds, may interact with capsule materials, or be incompatible with capsule materials. Such interactions, incompatibilities, and instabilities may lead to degradation of the heteroaryl-fused azadecalin compounds, reduce their bioavailability, or otherwise reduce their utility for therapeutic purposes. For these reasons, and others, pharmaceutical formulations for use in pills, tablets, solutions for injection, and other pharmaceutical formulations often may be unsuitable for therapeutic use.

Accordingly, improved formulations including heteroaryl-ketone fused azadecalin compounds having improved stability and/or bioavailability are needed.

SUMMARY

Applicant discloses herein formulations comprising the heteroaryl-ketone fused azadecalin (HKFA) compound (R)-(1-(4-fluorophenyl)-6((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (Example 18 of U.S. Pat. No. 8,859,774), also known as "relacorilant" and as "CORT125134", which has the following structure:

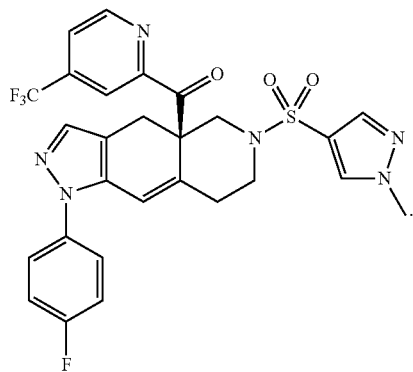 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

In embodiments, the formulations disclosed herein are suitable for pharmaceutical use, and have improved stability and/or bioavailability as compared to prior or alternative formulations. In embodiments, the formulations may include relacorilant and a pharmaceutically acceptable excipient. In embodiments, the formulations contain relacorilant and a pharmaceutically acceptable excipient and are suitable for use in pharmaceutical compositions for oral administration of relacorilant to human patients for treating a disease or disorder, or to animals for veterinary therapeutic purposes.

In embodiments, the pharmaceutical formulation is suitable for the administration of an effective amount of relacorilant, e.g., in a unit dose formulation containing between about 1 and about 1000 milligrams (mg) of relacorilant, or between about 1 and about 500 mg of relacorilant. In embodiments, unit dose formulations contain 10 mg, or 20 mg, or 25 mg, or 50 mg, or 100 mg, or 200 mg, or 300 mg, or 400 mg, or 500 mg relacorilant. In embodiments, the pharmaceutical formulation is suitable for the administration of an effective amount of relacorilant, e.g., a daily dose of relacorilant of between about 1 and 100 mg/kg/day, or a daily dose of relacorilant of between about 1 and 20 mg/kg/day.

In embodiments, the pharmaceutical formulation comprising relacorilant is suitable for administration when encapsulated in a gelatin capsule. In embodiments, the pharmaceutical formulation comprising relacorilant is suitable for administration when encapsulated in a soft gelatin ("softgel") capsule.

The formulation comprising relacorilant may contain, for example, about 5 to about 35% relacorilant, about 45% to about 75% surfactant, about 5 to about 35% solubilizer, and may include an antioxidant. In embodiments, the formulation comprising relacorilant may contain, for example, about 10 to about 30% relacorilant, about 50% to about 70% surfactant, about 10 to about 30% solubilizer, and may include an antioxidant. In embodiments, the formulation comprising relacorilant may contain, for example, about 12 to about 28% relacorilant, about 52% to about 68% surfactant, about 12 to about 28% solubilizer, and may include an antioxidant. In further embodiments the formulation may have the following composition: about 15% to 25% relacorilant, about 55% to 65% surfactant, and about 15% to 25% solubilizer, optionally including an antioxidant. In yet further embodiments, the formulation may have the following composition: about 20% relacorilant, about 60% surfactant, about 20% solubilizer, and about 0.02% antioxidant. In particular embodiments, the formulation may have the following composition: about 20% relacorilant, about 60% polyoxyl glyceride, about 20% propylene glycol compound, and about 0.02% antioxidant. In further particular embodiments, the formulation may have the following composition: about 20% relacorilant, about 60% lauryl polyoxyl-32 glycerides, about 20% propylene glycol monocaprylate, and about 0.02% antioxidant (e.g., butylated hydroxytoluene (BHT), buylated hydroxyanisole (BHA), tert-butyl hydroquinone (TBHQ), a tocopherol, a gallate, or other antioxidant).

In embodiments, the capsule containing the relacorilant-containing formulation may be a softgel capsule. Softgel capsules for containing a relacorilant-containing formulation may be made of about 50% to about 75% gelatin and about 25% to about 50% of a plasticizer (e.g., a sorbitol/glycerin blend), with purified water and/or colorants included as needed; and may be made of about 58% to about 68% gelatin and about 30% to about 42% plasticizer, or may be made of about 60% to about 70% gelatin and about 30% to about 40% of a plasticizer, or about 63% to about 65% gelatin and about 35% to about 37% of a plasticizer, or about 64% gelatin and about 36% plasticizer, with purified water and/or colorants included as needed. In embodiments, a batch of material for making softgel capsules for containing a relacorilant-containing formulation may be made, for example, of 195.05 g gelatin and 111.46 g of a sorbitol/glycerin blend, with purified water and/or colorants included as needed.

In further exemplary embodiments, Applicant discloses softgel capsules containing relacorilant; the softgel capsules containing relacorilant may be any softgel capsule as disclosed herein containing any relacorilant formulation disclosed herein. In embodiments, the softgel capsules containing relacorilant formulations may be made of about 63% to about 65% gelatin and about 35% to about 37% of a plasticizer, or about 64% gelatin and about 36% plasticizer, with purified water and/or colorants included as needed. The plasticizer may be, for example, a sorbitol/glycerin blend. The relacorilant held in the softgel capsule may be in any formulation described herein. In embodiments, the softgel capsule containing relacorilant contains a relacorilant formulation of about 15 to about 25% relacorilant, about 50% to about 70% surfactant, about 15 to about 25% solubilizer, and may include an antioxidant. In embodiments, the softgel capsule containing relacorilant contains a relacorilant formulation comprising about 20 relacorilant, about 60% surfactant, about 20% solubilizer, and may include an antioxidant.

In embodiments, the formulations disclosed herein are suitable for use in the treatment of disorders characterized by cortisol excess. In embodiments, the formulations disclosed herein are suitable for use in the treatment of Cushing's syndrome, including Cushing's Disease. In embodiments, the formulations disclosed herein are suitable for use in the treatment of other disorders. In embodiments of such treatment methods, pharmaceutical compositions comprising relacorilant may be administered alone, or may be administered in combination with other treatments for such diseases and disorders.

Many HKFA compounds are difficult to dissolve, difficult to formulate with pharmaceutically acceptable excipients, and are unstable (i.e., degrade by unacceptable amounts over time) in many formulations. Applicant discloses herein novel relacorilant-containing formulations and pharmaceutical compositions, with improved stability as compared to alternative formulations and compositions which are suitable for administration to human subjects. The novel formulations disclosed herein are believed to allow the safe and effective administration of relacorilant to patients suffering from diseases and disorders amenable to treatment by GRMs such as relacorilant. The formulations disclosed herein provide advantages including improved stability and compatibility with capsules suitable for oral administration, providing improved relacorilant formulations, and treatments using such improved relacorilant-containing formulations, as compared to alternative formulations and compositions.

DETAILED DESCRIPTION

Figure 1:
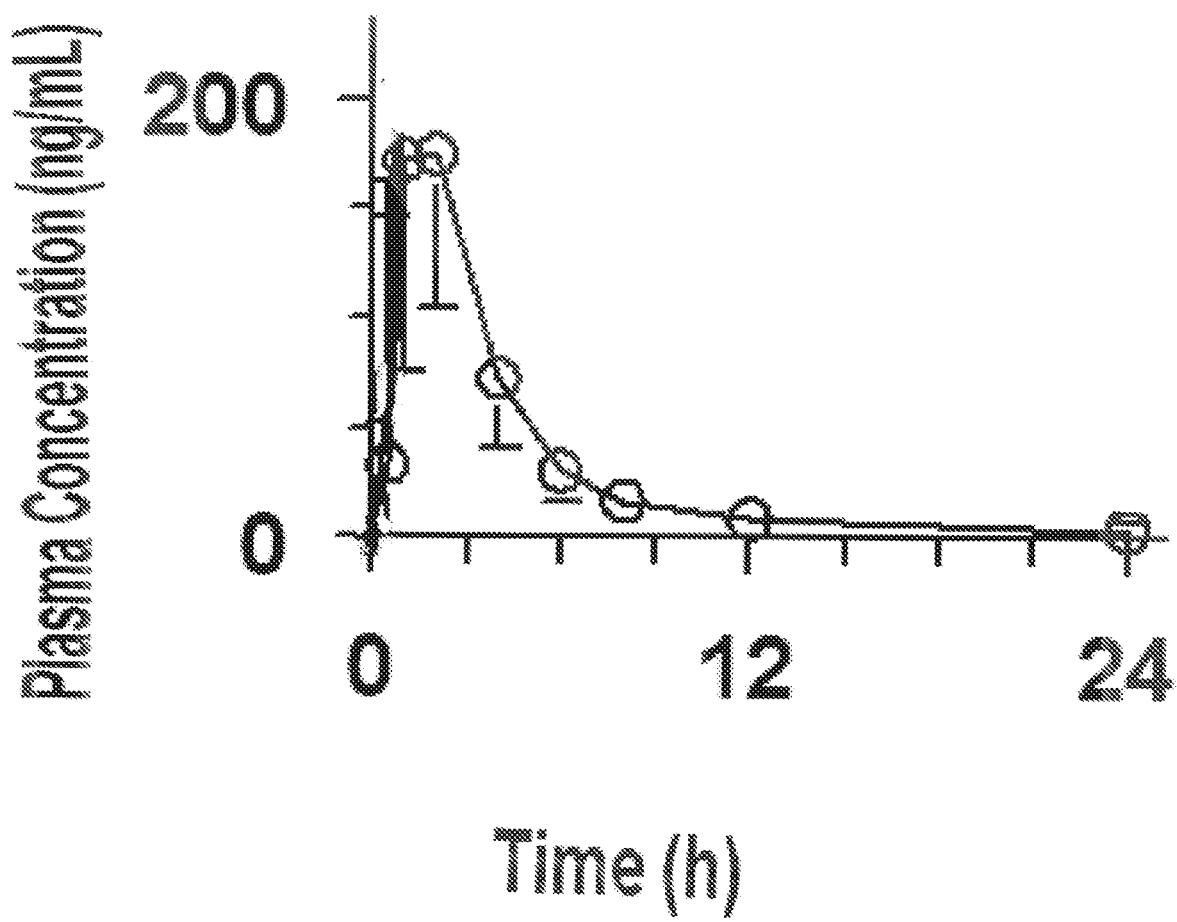
FIG. 1 shows the plasma concentration of relacorilant in healthy, fasted human subjects at times after ingestion of 150 mg relacorilant (provided in softgel capsules containing the formulation of Table III). The $C_{max}$ was nearly 200 ng/mL at its peak about 3 hours after administration (open circles; eight subjects were tested with this composition; the subjects were fasted when they were orally administered the relacorilant formulation).

Many fused azadecalin compounds are difficult to formulate, and many fused azadecalin compounds are unstable over time in formulations that are suitable for oral administration. Thus, development of stable and bioavailable formulations containing fused azadecalin compounds is an important challenge that it is necessary to overcome in order to provide improved fused azadecalin formulations suitable for human administration. Preferred embodiments entail the development of stable and bioavailable formulations containing fused azadecalin compounds suitable for oral administration to human patients.

Applicant has surprisingly developed multiple formulations which allow the incorporation of the heteroaryl-ketone fused azadecalin (HKFA) compound "relacorilant" into pharmaceutical compositions suitable for oral administration to patients. Relacorilant is (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, and has the following structure:

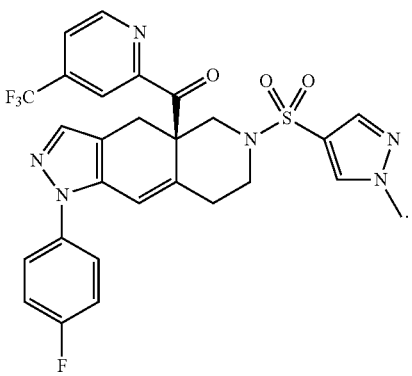 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

(Example 18 of U.S. Pat. No. 8,859,774)

These relacorilant-containing formulations provide improved stability and improved compatibility with capsules as compared to other, prior or alternative, relacorilant-containing formulations.

Disclosed herein are novel formulations and novel pharmaceutical compositions containing relacorilant. In embodiments, the formulations may include relacorilant and a pharmaceutically acceptable excipient, such as, e.g., a solubilizer, a surfactant, an antioxidant, a filler, or one or more other excipient. In embodiments, solubilizers such as, e.g., glycerols including glycerol caprylates, polyethylene or polypropylene glycerols, (commercially available as, e.g., Capmul ECM (glycerol caprate)) and surfactants such as polyethoxylated castor or other oils, (commercially available as, e.g., Kolliphor EL), may provide superior pharmaceutical formulations as compared to prior or alternative formulations. In embodiments, such formulations comprising HKFA compounds may also include antioxidants, e.g., butylated hydroxytoluene (BHT), butylated hydroxyanisole (BHA), tert-butyl hydroquinone (TBHQ), a gallate such as propyl gallate, a tocopherol such as alpha tocopherol, or other antioxidant.

In embodiments, Applicant discloses herein gelatin ("softgel") capsule formulations suitable for use in encapsulating relacorilant-containing formulations. Softgel capsules for containing a relacorilant-containing formulation may be made of about 50% to about 75% gelatin and about 25% to about 50% of a plasticizer, with purified water and/or colorants included as needed; and may be made of about 60% to about 70% gelatin and about 30% to about 40% of a plasticizer, or about 63% to about 66% gelatin and about 34% to about 37% of a plasticizer, with purified water and/or colorants included as needed. In embodiments, a batch of material for making softgel capsules for containing a relacorilant-containing formulation may be made, for example, of 195.05 g gelatin and 111.46 g of a sorbitol/glycerin blend plasticizer. In embodiments, the gelatin capsule may contain purified water as needed, and may further contain colorants as needed, if desired.

In embodiments, Applicant discloses herein relacorilant-containing formulations, including without limitation the following formulations ("%" is taken as weight percent herein):

a formulation comprising about 10 to about 30% relacorilant, about 50% to about 70% surfactant, about 10 to about 30% solubilizer, and optionally including an antioxidant;

a formulation comprising about 15 to about 25% relacorilant, about 55% to about 65% surfactant, about 15 to about 25% solubilizer, and optionally including an antioxidant;

a formulation comprising about 18% to 22% relacorilant, about 56% to 64% surfactant, and about 18% to 22% solubilizer, optionally including an antioxidant;

a formulation comprising about 20% relacorilant, about 60% surfactant, about 20% solubilizer, and about 0.1 to about 0.5% antioxidant;

a formulation comprising about 20% relacorilant, about 60% polyoxyl glyceride compounds, about 20% propylene glycol compounds, and about 0.02% BHT or BHA; and a formulation comprising about 20% relacorilant, about 60% Lauroyl polyoxyl-32 glycerides, about 20% propylene glycol monocaprylate, and about 0.02% BHT or BHA.

In embodiments, Applicant discloses herein relacorilant-containing formulations, including without limitation the following formulations, provided below in the amounts contained in a single capsule (e.g., a softgel capsule):

A formulation containing 25 mg relacorilant, 74.975 mg Lauroyl poloxyl-32 glycerides, 25 mg Propylene glycol monocaprylate, type I, and 0.025 mg Butylated hydroxytoluene (BHT);

A formulation containing 50 mg relacorilant, 149.95 mg Lauroyl poloxyl-32 glycerides, 50 mg Propylene glycol monocaprylate, type I, and 0.05 mg Butylated hydroxytoluene (BHT);

A formulation containing 100 mg relacorilant, 299.9 mg Lauroyl poloxyl-32 glycerides, 100 mg Propylene glycol monocaprylate, type I, and 0.1 mg Butylated hydroxytoluene (BHT);

A formulation containing 200 mg relacorilant, 599.8 mg Lauroyl poloxyl-32 glycerides, 200 mg Propylene glycol monocaprylate, type I, and 0.2 mg Butylated hydroxytoluene (BHT);

A formulation containing 300 mg relacorilant, 899.7 mg Lauroyl poloxyl-32 glycerides, 300 mg Propylene glycol monocaprylate, type I, and 0.3 mg Butylated hydroxytoluene (BHT);

A formulation containing 400 mg relacorilant, 1199.6 mg Lauroyl poloxyl-32 glycerides, 400 mg Propylene glycol monocaprylate, type I, and 0.4 mg Butylated hydroxytoluene (BHT);

A formulation containing 500 mg relacorilant, 1499.5 mg Lauroyl poloxyl-32 glycerides, 500 mg Propylene glycol monocaprylate, type I, and 0.5 mg Butylated hydroxytoluene (BHT);

A formulation containing 750 mg relacorilant, 2249.25 mg Lauroyl poloxyl-32 glycerides, 750 mg Propylene glycol monocaprylate, type I, and 0.75 mg Butylated hydroxytoluene (BHT);

A formulation containing 1000 mg relacorilant, 2999 mg Lauroyl poloxyl-32 glycerides, 1000 mg Propylene glycol monocaprylate, type I, and 1 mg Butylated hydroxytoluene (BHT); and other formulations with the same proportions. In order to determine the amounts of a further formulation with the same proportions having a different amount of relacorilant X, one must determine the ratio of X to 100 mg relacorilant, and multiply the ingredient amounts of the formulation above containing 100 mg relacorilant by that ratio. For example, where the further formulation includes 800 mg relacorilant, the ratio of 800 mg relacorilant:100 mg relacorilant is 8, and the amounts for each ingredient of the formulation including 100 mg relacorilant would be multiplied by 8.

In embodiments, Applicant discloses herein single unit dosage forms containing relacorilant, including without limitation the following single unit dosage forms:
a single unit dosage form consisting of a capsule containing a uniform admixture of between about 10 milligrams (mg) and about 70 mg of relacorilant and pharmaceutically acceptable excipients, wherein said uniform admixture is a formulation as disclosed herein, including, e.g., a formulation disclosed above; and
a single unit dosage form consisting of a capsule containing a uniform admixture of between about 20 milligrams (mg) and about 50 mg of relacorilant and pharmaceutically acceptable excipients, wherein said uniform admixture is a formulation as disclosed herein, including, e.g., a formulation disclosed above.
a single unit dosage form consisting of a capsule containing a uniform admixture of between about 50 milligrams (mg) and about 200 mg of relacorilant and pharmaceutically acceptable excipients, wherein said uniform admixture is a formulation as disclosed herein, including, e.g., a formulation disclosed above.
a single unit dosage form consisting of a capsule containing a uniform admixture of between about 100 milligrams (mg) and about 400 mg of relacorilant and pharmaceutically acceptable excipients, wherein said uniform admixture is a formulation as disclosed herein, including, e.g., a formulation disclosed above.
a single unit dosage form consisting of a capsule containing a uniform admixture of between about 200 milligrams (mg) and about 500 mg of relacorilant and pharmaceutically acceptable excipients, wherein said uniform admixture is a formulation as disclosed herein, including, e.g., a formulation disclosed above.
In embodiments, the contents of a single unit dosage form as disclosed herein, including as disclosed above, weighs between about 300 milligrams (mg) and about 600 mg. In embodiments, the contents of a single unit dosage form as disclosed herein, including as disclosed above, has a total weight of about 300 mg; or about 400 mg; or about 500 mg; or about 600 mg; or about 700 mg; or about 800 mg; or about 900 mg; or about 1 gram (g); or about 1.5 g; or about 2 g. In embodiments, the single unit dosage form is enclosed in a softgel capsule. In yet other embodiments, the single unit dosage form is enclosed in a hardshell capsule, which may have a size selected from, e.g., size 5, size 4, size 3, size 2, size 1, size 0, size 00, and size 000.

Relacorilant binds to the glucocorticoid receptor (GR), and is a GR modulator (GRM). Relacorilant GR modulation comprises antagonizing binding of other ligands, such as, e.g., cortisol, to a GR, and thus relacorilant is a GR antagonist (GRA). Since relacorilant binds well to GR, but binds only poorly to the progesterone receptor (PR) and to other steroid hormone receptors, relacorilant may be termed a selective GR modulator (SGRM). The novel pharmaceutical compositions disclosed herein are useful, for example, by providing pharmaceutical compositions for modulating a GR while not significantly affecting a PR.

In embodiments, the relacorilant-containing formulations may, as one of their effects, reduce harmful effects of excessive cortisol levels in subjects to which they have been administered. In embodiments, the relacorilant-containing formulations may, as one of their effects, be effective to treat disorders in subjects to which they have been administered. In embodiments, the relacorilant-containing formulations may, as one of their effects, be effective to enhance the action of co-administered drugs or therapies in the treatment of disorders in subjects to which they have been administered, where co-administered drugs or therapies may be administered close in time to, at a time or times prior to, at the same time as, or following administration of the relacorilant-containing formulations.

In embodiments, Applicant discloses herein methods of treating conditions amenable to treatment with relacorilant, including without limitation the following methods:
a method of treating a condition amenable to treatment by relacorilant comprising administering relacorilant in a single unit dosage form, wherein said single unit dosage form contains a uniform admixture of said relacorilant and pharmaceutical excipients, and wherein said uniform admixture is a formulation as disclosed herein. In embodiments of the methods disclosed herein, the single unit dosage form consists of a capsule containing between about 10 milligrams (mg) and about 500 mg of relacorilant.

In embodiments of the methods disclosed herein, the single unit dosage form consists of a capsule containing a uniform admixture of between about 5 milligrams (mg) and about 500 mg of relacorilant. In embodiments of the methods disclosed herein, the single unit dosage form consists of a capsule containing a uniform admixture of between about 10 milligrams (mg) and about 250 mg of relacorilant. In embodiments of the methods disclosed herein, the single unit dosage form consists of a capsule containing a uniform admixture of between about 20 milligrams (mg) and about 150 mg of relacorilant.

In embodiments, the pharmaceutical composition comprising relacorilant is formulated for oral administration. In embodiments, the oral administration comprises sublingual administration. In embodiments the HKFA compound is formulated for administration as a suppository, and may be administered rectally or intravaginally.

B. Definitions

The abbreviations used herein have their conventional meaning within the chemical and biological arts.

As used herein, the term "compound" is used to denote a molecular moiety of unique, identifiable chemical structure. A compound may exist in a free species form, in which it is not associated with other molecules. A compound may also exist as part of a larger aggregate, in which it is associated with other molecule(s), but nevertheless retains its chemical identity. A solvate, in which the compound is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

"Patient", "subject", "subject in need" and the like refer to a person having, or suspected of having, a disease or condition which may be treated by administration of a therapeutic drug.

As used herein, the terms "administer," "administering," "administered" or "administration" refer to providing a compound or a composition (e.g., one described herein), to a subject or patient.

As used herein, the term "administration" refers to the delivery of a drug or other therapeutic into the body of a subject in need of treatment by the drug or therapeutic, effective to achieve a therapeutic effect. Administration may be by any suitable route of administration, including, for example, oral administration; intravenous administration; subcutaneous administration; parenteral administration; intra-arterial administration; nasal administration; topical administration; and other routes of administration.

"Treat", "treating" and "treatment" refers to providing a drug or other therapeutic agent to a patient. Such treatments are intended to, and typically result in reduction of symptoms, or amelioration of symptoms, or abatement of symptoms, or abolition of symptoms, of the disease or disorder to be treated. Such treatments are intended to, and typically result in, an indication of success in the treatment or amelioration of a pathology or condition. Indicia of success include, e.g., any objective or subjective parameter such as abatement; remission; diminishing of symptoms or making the pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters; including the results of a physical examination; histopathological examination (e.g., analysis of biopsied tissue); laboratory analysis of urine, saliva, tissue samples, serum, plasma, or blood; or imaging.

As used herein, the term "Cushing's syndrome" refers to an array of symptoms caused by excess cortisol (excess cortisol is termed "hypercortisolism"). "Cushing's Disease" refers to pituitary-dependent Cushing's syndrome, e.g., excess cortisol caused by pituitary abnormality (typically a pituitary tumor). Symptoms associated with, and indicative of, Cushing's syndrome include, for example, elevated blood pressure (hypertension), elevated blood glucose (hyperglycemia), increased weight (typically in the mid-section, and in the face causing a characteristic "moon-face"), immune suppression, thin skin, acne, depression, hirsutism, and other symptoms. The excess cortisol that leads to Cushing's syndrome may be due to exogenous cortisol (or cortisol analog such as prednisone, cortisone, dexamethasone, or other cortisol analog or cortisol mimetic); may be due to a pituitary tumor; may be due to an adrenal tumor or other adrenal disease; may be due to a tumor not located in or near to the pituitary or an adrenal gland; or may be due to another cause. In some cases, a Cushing's syndrome patient may refuse surgery, or surgery may have failed to cure the disease or relieve the symptoms; a GRM, such as relacorilant, is often useful in treating such patients.

A condition associated with Cushing's syndrome may be, without limitation, a condition associated with endogenous Cushing's syndrome; hyperglycemia secondary to hypercortisolism; hypercortisolism associated with, or causing, type 2 diabetes mellitus or glucose intolerance; hyperglycemia secondary to hypercortisolism associated with, or caused by, type 2 diabetes mellitus or glucose intolerance.

The term "glucocorticosteroid" or "glucocorticoid" (both abbreviated GC) refers to a steroid hormone or synthetic analog that binds to a glucocorticoid receptor. Glucocorticosteroids are typically characterized by having 21 carbon atoms, an $\alpha,\beta$-unsaturated ketone in ring A, and an $\alpha$-ketol group attached to ring D. They differ in the extent of oxygenation or hydroxylation at C-11, C-17, and C-19; see Rawn, "Biosynthesis and Transport of Membrane Lipids and Formation of Cholesterol Derivatives," in Biochemistry, Daisy et al. (eds.), 1989, pg. 567.

As used herein, the term "glucocorticoid receptor" ("GR") refers to a family of intracellular receptors which specifically bind to cortisol and/or cortisol analogs. The glucocorticoid receptor is also referred to as the cortisol receptor. The term includes isoforms of GR, recombinant GR and mutated GR. "Glucocorticoid receptor" ("GR") refers to the type II GR which specifically binds to cortisol and/or cortisol analogs such as dexamethasone (See, e.g., Turner & Muller, J. Mol. Endocrinol. Oct. 1, 2005 35 283-292).

As used herein, the terms "effective amount," "amounts effective," therapeutic amount", and "therapeutically effective amount" refer to an amount or amounts of one or more pharmacological agents effective to treat, eliminate, or mitigate at least one symptom of the disease being treated. In some cases, "effective amount," "amounts effective," "therapeutic amount", and "therapeutically effective amount" can refer to an amount of a functional agent or of a pharmaceutical composition useful for exhibiting a detectable therapeutic or inhibitory effect. The effect can be detected by any assay method known in the art.

As used herein, the term "consisting essentially of", as related to a list of ingredients in a formulation, refers to the recited ingredients, where the formulation may also include any unlisted ingredients that would not materially affect the utility of the formulation.

As used herein, the terms "excipient", "pharmaceutically acceptable excipient", and "pharmaceutically acceptable carrier" are used interchangeably to refer to any compound or material which is included in a formulation or in a pharmaceutical composition other than the active ingredient (or active ingredients where more than one compound may have the desired pharmaceutical activity). An excipient may serve as, e.g., a solvent, solubilizer or solubility enhancer; an emulsifier; a bulking agent; a stabilizer; a diluent; a surfactant; a preservative; a colorant; a flavor; a filler; a lubricant; or other agent which may serve other functions. Non-limiting examples of excipients include water, sodium chloride (NaCl), normal saline solutions, lactated Ringer's, normal sucrose, normal glucose, binders, fillers, disintegrants, lubricants, coatings, sweeteners, flavors and colors, and the like. As used herein, these terms are intended to include any and all solvents, dispersion media, coatings, antibacterial and antifungal agents, isotonic and absorption delaying agents, and the like, compatible with pharmaceutical administration. One of skill in the art will recognize that other pharmaceutical excipients are useful in the present invention, and their use is well known in the art. Any such pharmaceutically-acceptable excipients may be used in the formulations disclosed herein is contemplated except insofar as an excipient is incompatible with the active compound. It will be understood that supplementary active compounds can also be incorporated into the compositions. It is understood that the pharmaceutically acceptable excipients are non-toxic. Additional information on suitable pharmaceutically acceptable excipients can be found in Remington's Pharmaceutical Sciences, 17th ed., Mack Publishing Company, Easton, Pa., 1985, which is incorporated herein by reference.

As used herein, "active pharmaceutical ingredient", "API", and variants thereof refer to the compound in a formulation or pharmaceutical composition that has therapeutic activity when administered to a patient. Although other ingredients may also have beneficial effects, the formulation or pharmaceutical composition is configured to, and has been developed for, delivery of the API in order to provide the therapeutic benefit of the API to the patient to whom it is administered, while any beneficial effects of other ingredients is incidental.

As used herein, the terms "formulation", "pharmaceutical formulation", "composition", "pharmaceutical composition", and the like are interchangeable and refer to compositions suitable for administration to a patient for treatment of a medical condition or for amelioration of symptoms of a medical condition. A pharmaceutical formulation as disclosed herein comprises an active ingredient (e.g., relacorilant), and an inert ingredient (e.g., a pharmaceutically acceptable excipient). In embodiments, a pharmaceutical formulation includes one or more active ingredients and one or more pharmaceutically acceptable excipients. A pharmaceutical formulation is suitable for administration to a patient; in embodiments, a pharmaceutical formulation is suitable for oral administration to a patient.

As used herein, the terms "percent" and "%" refer to a percentage taken by comparing a first value to a second value, and multiplying the resulting decimal fraction by 100. As used herein, the first value may be the weight of an ingredient in a formulation containing multiple ingredients, and the second value may be the weight of all ingredients (i.e., the total weight of the formulation). Thus, for example, where the weight of a relacorilant dose in a pharmaceutical formulation containing that relacorilant is 100 milligrams (mg), and the total weight of all the ingredients in the formulation is 400 mg, then relacorilant makes up 25% of the formulation.

As used herein, the terms "weight percent", "weight %", "(% w/w)" and the like refer to the percentage of an ingredient of a composition with respect to the total weight of a composition containing at least two ingredients.

As used herein, the phrase "between about x % and about y %" (where x and y may be any number) is used inclusively, so that the range include the number values stated and all values between those minimum and maximum values.

As used herein, the phrases "unit dosage form" and "single unit dosage form" refer to formulations contained in pills, capsules, and other enclosures that are suitable for administration to a patient. The dosage (i.e., the amount of API) in a unit dosage form is fixed, and allows standardization of administration, without requiring measurement of the API or formulation by a patient or healthcare practitioner. Doses administered to a patient may be increased by administration of multiple pills, capsules, etc. In some cases, fractional doses may be administered, e.g., by cutting a pill in two or more pieces.

In embodiments, relacorilant-containing formulations disclosed herein may be suitable for oral administration.

Pharmaceutical formulations may be contained in capsules for administration of pharmaceutical ingredients, such as relacorilant, to patients for therapeutic purposes. In embodiments, such capsules are suitable for administration pharmaceutical ingredients, such as relacorilant, in unit doses to patients.

Formulations

Heteroaryl-ketone fused azadecalin (HKFA) compounds may be useful in formulations as disclosed herein, including in formulations suitable for oral administration (see, e.g., U.S. Pat. No. 8,859,774, the entire contents of which is hereby incorporated by reference in its entirety). Relacorilant is an exemplary HKFA compound, and formulations which provide relacorilant in a form suitable for oral administration to a patient are useful. Relacorilant is (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (Example 18 of U.S. Pat. No. 8,859,774), also known as "CORT125134", and has the following structure:

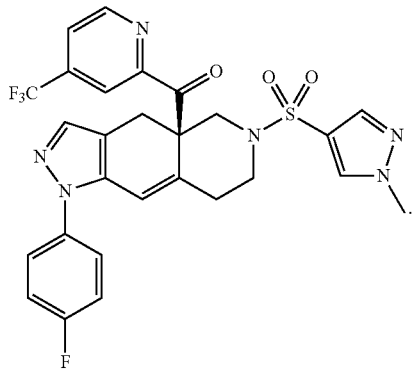 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Formulations suitable for administration to patients, and, in embodiments, suitable for oral administration to patients, may include relacorilant in proportions of between about 1% and about 50% by weight; in embodiments, such formulations may include relacorilant in proportions of between about 5% and about 35% by weight; in embodiments, such formulations may include relacorilant in proportions of between about 10% and about 30% by weight; in embodiments, such formulations may include relacorilant in proportions of between about 15% and about 25% by weight; in further embodiments, such formulations may include relacorilant in proportions of between about 17% and about 23% by weight; and in further embodiments, such formulations may include relacorilant in proportions of between about 19% and about 21% by weight; and in embodiments, such formulations contain about 20% relacorilant by weight.

Accordingly, Applicant discloses herein compositions comprising relacorilant may be useful in treating patients suffering from a condition amenable to treatment with relacorilant, and may be used in the treatment of a patient in need of such treatment. Conditions amenable to treatment with relacorilant may include without limitation, any of the conditions, disorders, and diseases disclosed herein (e.g., see supra), including for example, Cushing's syndrome, Cushing's Disease, diabetes, hyperglycemia and other disorders.

For preparing pharmaceutical compositions from the compounds of the present invention, pharmaceutically acceptable excipients can be either solid or liquid. Preparations may include formulations incorporated into, or contained by, tablets, pills, capsules, cachets, or suppositories. An excipient can be one or more substances, which may also act as diluents, flavoring agents, binders, preservatives, tablet disintegrating agents, or an encapsulating material, as disclosed herein (e.g., supra). Details on techniques for formulation and administration are well described in the scientific and patent literature, see, e.g., the latest edition of Remington's Pharmaceutical Sciences, Mack Publishing Co, Easton Pa. ("Remington's").

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Formulations as disclosed herein may comprise excipients and other components known in the art to be suitable for use in pharmaceutical compositions for administration to humans. Such excipients and components include, without limitation, surfactants, solubilizers, antioxidants, fillers, and other components. For example, suitable commercially available excipients and components include, without limitation, Capmul ECM (glycerol caprate); Kolliphor EL (polyethoxylated castor oil); Kolliphor EM; Gelucire 44/14 (lauroyl polyoxyl-32 glycerides); Capryol PGMC (propylene glycol monocaprylates); polysorbate 20; polysorbate 80; sorbitol/glycerin blend (e.g., the "50/50 Blend Sorbitol Special™" commercially available from SPI Pharma, Septemes, FR); corn oil; lauroglycol 90; butylated hydroxytoluene (BHT); butylated hydroxyanisole (BHA); tert-butyl hydroquinone (TBHQ); propyl gallate; alpha-tocopherol (vitamin E); myristic acid; and others.

Surfactants

As used herein, the term "surfactant" refers to, without limitation, polysorbate (polyoxyethylene sorbitan monolaureate) surfactants and detergents (such as, e.g., Tween® 20, Tween® 80, and others); may include polyoxyl glycerides, e.g., lauryl polyoxyl glycerides and other polyoxyl glycerides, and may include ionic, and non-ionic surfactants.

Formulations suitable for administration, including oral administration, to a patient and containing relacorilant may include a surfactant, including a non-ionic surfactant, in proportions of between about 10% and about 90% by weight; in embodiments, such formulations and compositions containing relacorilant may include surfactant, including a non-ionic surfactant, in proportions of between about 15% and about 80% by weight; in embodiments, such formulations and compositions containing relacorilant may include surfactant, including a non-ionic surfactant, in proportions of between about 20% and about 75% by weight; and in embodiments, such formulations and compositions containing relacorilant may include surfactant, including a non-ionic surfactant, in proportions of between about 25% and about 70% by weight. In embodiments, such formulations and compositions containing relacorilant may not include a non-ionic surfactant. In embodiments, such formulations and compositions containing relacorilant may not include a surfactant.

Surfactants, including non-ionic surfactants, are used as excipients. Surfactant excipients suitable for use in formulations as disclosed herein may include non-ionic surfactants, including sorbitan surfactants such as sorbitan monooleate; polysorbates (of many sizes, including e.g., polysorbate 20, polysorbate 80, also known as Tween® 20 and Tween® 80 as discussed above); and other non-ionic surfactants including, e.g., those sold as Cremophor® or Kolliphor® (e.g., Cremophor® EL, Kolliphor® EL, Cremophor® RH 40, Cremophor® RH 60, etc.), d-α-tocopherol, Solutol HS 15, poloxamer 407, Labrafil® M-1944CS (Gattefosse), Labrafil M-2125CS (Gattefosse), Labrasol® (Gattefosse, Saint-Priest, Lyon, France), Softigen® 767), and other surfactants known in the art.

For example, polysorbate (polyoxyethylene sorbitan monolaureate) surfactants and detergents (such as, e.g., Tween® 20, Tween® 80, and others, where numbers such as "20" and "80" indicate the numbers of repeating polyethylene glycol units in the polymers) are used as excipients in formulating pharmaceuticals, and aid in the emulsification and/or solubilization of active compounds in addition to their actions as surfactants. Such nonionic detergents and surfactants are available, e.g., from SIGMA-Aldrich, St. Louis, MO, USA.

In embodiments, relacorilant-containing formulations as disclosed herein may include Gelucire (e.g., Gelucire® 44/14, available from Gattefosse, Saint-Priest, Lyon, France) as a surfactant.

In embodiments, relacorilant-containing formulations as disclosed herein may include a "Kolliphor" as a surfactant. Kolliphor® EL (also known as cremophor; see above) is a polyethoxylated castor oil used as a non-ionic oil-in-water emulsifier. Kolliphor P188 is a poloxamer. Kolliphor® HS 15 (polyethylene glycol (15)-hydroxystearate is a solubilizer/emulsifier. Kolliphor® RH40 is Macrogolglycerol hydroxystearate. These materials are available from SIGMA-Aldrich, St. Louis, MO, USA.

Solubilizers

Formulations suitable for administration, including oral administration, to a patient and containing relacorilant may include a solvent, solubilizer, or solubility enhancer, or a plurality of solvents, solubilizers, or solubility enhancers in proportions of between about 2% and about 90% by weight; in embodiments, such formulations and compositions containing relacorilant may include a solvent, solubilizer, or solubility enhancer, or a plurality thereof, in proportions of between about 3% and about 80% by weight; or, in embodiments, in proportions of between about 5% and about 70% by weight; or in embodiments, in proportions of between about 8% and about 60% by weight; or, in further embodiments, in proportions of between about 10% and about 50% by weight. In embodiments, such formulations and compositions containing relacorilant may not include a solvent.

As used herein, the term "solubilizer" refers, without limitation, to solubilizers such as, e.g., polyethylene glycols (PEG), ethanol, propylene glycols, glycerols, glycerin, N-methyl-2-pyrrolidone, dimethylacetamide, dimethylsulfoxide, other water-soluble organic solvents, and other solubilizers known in the art. In embodiments, a solubilizer may be, e.g., a propylene glycol or propylene glycol ester, such as, e.g., a propylene glycol caprylate (e.g., a propylene glycol monocaprylate).

Polyethylene glycols of many forms, and derivatives thereof, are useful as solubilizers, and are useful in other ways, in the formulations disclosed herein. For example, PEG may have mean molecular weight of 300 kD or 400 kD (e.g., polyethylene glycol 300, polyethylene glycol 400); may be used in succinate form as polyethylene glycol (PEG) succinates (e.g., polyethylene glycol 1000 succinate) and in the form of mono- and di-fatty acid esters of PEG (e.g., PEG 300, 400, and 1750 mono- and di-fatty acid esters); and in other forms. Polyethylene glycols of a wide range of molecular weights (e.g., PEG300 which has an average molecular weight of about 300 grams per mole, and PEG400 which has an average molecular weight of about 400 grams per mole) are available, e.g., from SIGMA-Aldrich, St. Louis, MO, USA.

Solvents, solubilizers, and solubility enhancers used as excipients in formulations as disclosed herein may also include ethanol, glycerin, N-methyl-2-pyrrolidone, dimethylacetamide, dimethylsulfoxide, and other water-soluble organic solvents. In embodiments, formulations as disclosed herein containing a HKFA may include diethylene glycol monoethyl ether (sold under the names Transcutol®, Carbitol®, dioxitol, and other names); Transcutol®, e.g., Transcutol® HP, is available from Gattefosse, Saint-Priest, Lyon, France.

Further Excipients

Excipients used in formulations as disclosed herein may include lipids and phospholipids, including naturally occurring lipid compositions such as, e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil). Excipients used in formulations as disclosed herein may also include phospholipids such as, e.g., phosphatidylcholine, distearoylphosphatidylglycerol L-α-dimyristoylphosphatidylcholine, L-α-dimyristoylphosphatidylglycerol, and other phospholipids. Lipids and phospholipids may be used, e.g., as emulsifiers, bulking agents, fillers, lubricants, and for other purposes.

In embodiments, formulations as disclosed herein containing a GRM may include triglycerides, including medium chain triglycerides. Medium chain triglycerides are triglycerides with fatty acid chain lengths of between about 6 to about 12 carbons long. Triglycerides may include, e.g., 1,2,3-triacetoxypropane (also known as triacetin or as glycerin triacetate). Triacetin is available, e.g., from SIGMA-Aldrich, St. Louis, MO, USA. Triglyceride excipients such as, triacetin, may serve, e.g., as solvents, as plasticizers, and as humectants.

Excipients used in formulations as disclosed herein may include various cyclodextrins such as, e.g., α-cyclodextrin, β-cyclodextrin, hydroxypropyl-β-cyclodextrin, sulfobutyle-ther-β-cyclodextrin, and others. Cyclodextrins may be used, e.g., as emulsifiers, solubilizers, and for other purposes.

Formulations Containing Relacorilant

In embodiments, relacorilant-containing formulations as disclosed herein may include Propylene Glycol Monocaprylate (sold, e.g., as Capryol™ 90 by Gattefosse, Saint-Priest, Lyon, France). In embodiments, relacorilant-containing formulations as disclosed herein may include Caprylocaproyl polyoxylglycerides such as Labrasol® (sold by Gattefosse, Saint-Priest, Lyon, France; see above).

In embodiments, formulations suitable for administration, including oral administration, to a patient and containing relacorilant may include a polyethylene glycol (PEG) in proportions of between about 5% and about 50% by weight; in embodiments, such formulations and compositions containing a GRM may include a PEG in proportions of between about 10% and about 40% by weight; and in embodiments, such formulations and compositions containing relacorilant may include a PEG in proportions of between about 15% and about 30% by weight.

In embodiments, formulations suitable for administration, including oral administration, to a patient and containing relacorilant may include a polysorbate (such as, e.g., Tween® 20 or Tween® 80) in proportions of between about 5% and about 75% by weight; and in embodiments, such formulations and compositions containing relacorilant may include a polysorbate in proportions of between about 20% and about 60% by weight. In embodiments, such formulations and compositions containing relacorilant may not include a polysorbate.

Excipients used in formulations as disclosed herein may include organic materials (which may be liquid or may be semi-solid at room temperature) such as, e.g., beeswax, a tocopherol (e.g., α-tocopherol (also termed vitamin E, or vitE)), oleic acid, gum Arabic, lanolin, starch, syrup, honey, and medium-chain mono- and diglycerides. Such organic materials may be used, e.g., as bulking agents, fillers, lubricants, and for other purposes.

In embodiments, relacorilant-containing formulations as disclosed herein may include Vitamin E (e.g., α-tocopherol and other tocopherols, including, e.g., α-tocopherol polyethylene glycol succinate (Vitamin E TPGS)). Vitamin E, including vitamin E TPGS, are available, e.g., from SIGMA-Aldrich, St. Louis, MO, USA. Vitamin E may serve, e.g., as a solubilizer; as an emulsifier; and as an antioxidant.

Further excipients and materials useful in formulations and in the manufacture of pharmaceuticals for administration, including pharmaceutical for oral administration, include sterile water for irrigation; ethanol; gelatin (e.g., edible gelatin, having a jelly strength measured in "bloom" units, such as Gelatin 220 Bloom); coatings such as hydroxypropyl methylcellulose (HPMC, "hypromellose", e.g., Pharmacoat® 603 and Pharmacoat® 615) and polyvinyl alcohol coating materials; and other materials.

Exemplary Formulations

Many GRMs, including many HKFA GRMs, are difficult to formulate in pharmaceutically acceptable formulations. Problems include poor solubility in water; poor solubility in solvents that may be used in pharmaceutical formulations; poor stability; light sensitivity; precipitation in physiological environments; low bioavailability; incompatabiity with pharmaceutically acceptable capsules and coatings; and other difficulties. Poor stability is a particular problem in developing formulations suitable for administration to patients in clinical practice.

Applicant discloses herein formulations which are believed to overcome such obstacles. Some embodiments of suitable formulations are presented in the Examples, and are also more generally described herein. For example, a formulation suitable for oral administration to humans and containing relacorilant may contain, for example, about 15% to about 25% relacorilant, about 50% to about 70% surfactant, about 15% to about 25% solubilizer, and may include a small but effective amount of antioxidant (e.g., less than about 0.1%), where % indicates % w/w. In another example, a formulation suitable for oral administration to humans and containing relacorilant may contain, for example, about 20% relacorilant, about 60% surfactant, about 20% solubilizer, and may optionally include a small but effective amount of antioxidant (e.g., less than about 0.1%), where % indicates % w/w.

In embodiments of such formulations, the surfactant may be a glyceride, such as a polyoxyl glyceride, such as, e.g., lauroyl polyoxyl-32 glyceride. In embodiments, the surfactant may be a polysorbate, such as, e.g., TWEEN 20 or TWEEN 80. It will be understood that other suitable surfactants are known to those of skill in the art, and may be used with, or used in place of, a polysorbate. It will be understood that other suitable surfactants are known to those of skill in the art.

In embodiments of such formulations, the solubilizer may include glycerol, or polyethylene glycol, or polypropylene glycol. In embodiments of such formulations, the surfactant may be a propylene glycol, such as propylene glycol monocaprylate, e.g., propylene glycol monocaprylate Type I. In embodiments of such formulations, the surfactant may be a glycerol caprate. In further embodiments of such formulations and pharmaceutical compositions, without limitation, the solubilizer may be one or more of an oil, such as corn oil, castor oil, and other oils; may be one or more of a polyethylene glycol (PEG), ethanol, propylene glycol, glycerin, N-methyl-2-pyrrolidone, dimethylacetamide, dimethylsulfoxide; and may include combinations thereof. It will be understood that other suitable solubilizers are known to those of skill in the art, and may be used with, or used in place of, the solubilizers recited herein.

In embodiments, an antioxidant is included in formulations containing relacorilant suitable for administration to humans. The antioxidant may be, for example, BHT, BHA, TBHQ, alpha-tocopherol (vitamin E), a gallate (such as, e.g., propyl gallate), or other antioxidant, and may comprise combinations thereof.

For example, embodiments of formulations containing relacorilant suitable for administration to humans may include one of more of the following commercially available ingredients: Capmul MCM; Kolliphor EL; Kolliphor ELP; Gelucire 44/14; Capryol PGMC; polysorbate 80; propyl gallate; BHT; BHA; alpha-tocopherol; myristic acid; and others.

In embodiments, a unit dosage of relacorilant is contained in a capsule, e.g., a softgel capsule, or a hardshell capsule. Formulations may be encapsulated in gelatin capsules; for example, in preferred embodiments, the capsules may be softgel capsules. Softgel capsules are typically prepared in a size suitable to accommodate their contents. Capsules are typically sized so as to accommodate from one or a few milligrams up to a several hundred milligrams of the active pharmaceutical ingredient (API), such as relacorilant. In embodiments, the amount of relacorilant contained in a softgel capsule may be about 10 mg, about 20 mg, about 30 mg, about 40 mg, about 50 mg, about 60 mg, about 70 mg, about 80 mg, about 100 mg, about 120 mg, about 140 mg, about 150 mg, about 170 mg, about 175 mg, about 180 mg, about 200 mg, about 225 mg, about 250 mg, about 300 mg, about 325 mg, about 350 mg, about 375 mg, about 400 mg, about 425 mg, about 450 mg, about 475 mg, about 500 mg, about 550 mg, about 600 mg, about 650 mg, about 700 mg, about 750 mg, about 800 mg, or more. Hardshell capsules may be chosen for a size that is suitable for holding the desired formulation, and may be, e.g., size 5 capsules, size 4 capsules; size 3 capsules; size 2 capsules; size 1 capsules; size 0 capsules; size 00 capsules; and other size capsules.

Administration

In embodiments, the formulation is suitable for the administration of an effective amount of relacorilant, e.g., in a unit dose formulation containing between about 1 and about 500 milligrams (mg) of relacorilant. In some embodiments, a unit dose relacorilant formulation is suitable for oral administration. In some embodiments, a unit dose relacorilant formulation may contain up to about 750 mg of relacorilant. In some embodiments, the unit dose of relacorilant is 1, 2, 4, 6, 8, 10, 12, 14, 16, 18, 20, 25, 30, 40, 50, 60, 70, 80, 90, 100, 150, 200, 250, 300, 350, 400, 450, 500, or 750 mg. In embodiments, the formulation comprising relacorilant is suitable for administration on a daily basis, or on a twice daily basis, or on a three times per day basis. In embodiments, the formulation comprising relacorilant is suitable for administration every other day, or every third day, or every fourth day, or every fifth day, or every sixth day, or on a once per week basis. In embodiments, the formulation comprising relacorilant is suitable for administration for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

In embodiments, the pharmaceutical formulation is suitable for the administration of an effective amount of relacorilant, e.g., a daily dose of relacorilant of between about 1 and 100 mg/kg/day, preferably between about 1 mg/kg/day and about 20 mg/kg/day. In some embodiments, the daily dose of relacorilant is 1, 2, 4, 6, 8, 10, 12, 14, 16, 18, 20, 30, 40, 50 60, 70, 80, 90 or 100 mg/kg/day. In embodiments, the relacorilant is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

In embodiments, the pharmaceutical formulation comprising relacorilant is suitable for administration when encapsulated in a gelatin capsule. In embodiments, the pharmaceutical formulation comprising relacorilant is suitable for administration when encapsulated in a soft gelatin ("softgel") capsule. In embodiments, such a softgel capsule is composed of about 50% to about 75% gelatin and about 25% to about 50% sorbitol/glycerin blend, and may also include purified water and/or colorants. In some embodiments, a unit dose relacorilant formulation is contained in a softgel capsule. An exemplary softgel capsule may be composed of the following ingredients:

| Component | Composition (mg) |
|---|---|
| Gelatin | 195.05 |
| Purified Water | As needed for gel mass preparation |
| Sorbitol/Glycerin Blend | 111.46 |
| Colorants | As needed |

Sorbitol/glycerin blend contains a 50:50 blend of sorbitol and glycerin.

In embodiments, the pharmaceutical formulation comprising relacorilant is suitable for administration with another pharmaceutical formulation, e.g., with a pill, tablet, oral solution, injectable, or other formulation including another active ingredient.

The formulations and methods disclosed herein may be useful in treating patients suffering from any condition amenable to treatment with a GRM, as discussed supra.

In embodiments, the pharmaceutical composition comprising relacorilant is formulated for oral administration. In embodiments, the oral administration comprises sublingual administration. In embodiments the relacorilant is formulated for administration as a suppository, and may be administered rectally or intravaginally.

Methods of treating diseases including without limitation, e.g., Cushing's syndrome, by administration of a GRM in such pharmaceutical compositions are also provided. In embodiments, a patient suffering from a disease or condition amenable to treatment by the GRM is administered a pharmaceutical composition disclosed herein; in embodiments, the administration comprises oral administration.

The relacorilant-containing pharmaceutical preparation is preferably in unit dosage form. In such form the preparation is subdivided into unit doses containing appropriate quantities of relacorilant. A unit dosage form may be, for example, a pill or capsule including or containing relacorilant.

In embodiments, a unit dosage form contains between about 0.1 milligram (mg) of relacorilant and about 750 mg of relacorilant; in further embodiments, a unit dosage form contains between about 1 mg of relacorilant and about 600 mg of relacorilant; in further embodiments, a unit dosage form contains between about 5 mg of relacorilant and about 500 mg of relacorilant; in further embodiments, a unit dosage form contains between about 10 mg of relacorilant and about 400 mg of relacorilant; in further embodiments, a unit dosage form contains between about 15 mg of relacorilant and about 350 mg of relacorilant; in further embodiments, a unit dosage form contains between about 20 mg of relacorilant and about 300 mg of relacorilant; in further embodiments, a unit dosage form contains between about 25 mg of relacorilant and about 250 mg of relacorilant.

In particular embodiments, the unit dosage form may contain between about 5 milligrams (mg) and about 200 mg relacorilant. In further embodiments, the unit dosage form may contain between about 10 mg and about 150 mg relacorilant. In yet further embodiments, the unit dosage form may contain between about 15 mg and about 100 mg relacorilant. In still further embodiments, the unit dosage form may contain between about 20 mg and about 80 mg relacorilant. In embodiments, the unit dosage form may contain between about 25 mg and about 75 mg relacorilant. In yet further embodiments, the unit dosage form may contain between about 30 mg and about 60 mg relacorilant.

In particular embodiments, the unit dosage form may contain about 10 mg of relacorilant; or about 25 mg of relacorilant; or about 40 mg of relacorilant; or about 50 mg of relacorilant; or about 75 mg of relacorilant; or about 100 mg of relacorilant; or about 125 mg of relacorilant; or about 150 mg of relacorilant; or about 200 mg of relacorilant; or about 250 mg of relacorilant; or about 300 mg of relacorilant; or about 350 mg of relacorilant; or about 400 mg of relacorilant; or about 450 mg of relacorilant; or about 500 mg of relacorilant; or about 550 mg of relacorilant; or about 600 mg of relacorilant; or about 650 mg of relacorilant; or about 700 mg of relacorilant; or about 750 mg of relacorilant; or about 800 mg of relacorilant.

The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The single unit dosage form containing relacorilant may be administered once a day, or two, three, or more times per day so as to provide the preferred dosage level per day. Multiple units of the single unit dosage form containing relacorilant may be administered at the same time, or on the same day, so as to achieve the desired dosage (amount of relacorilant) per day.

The composition can also contain other compatible therapeutic agents. The compounds described herein can be used in combination with one another, or with adjunctive agents that may not be effective alone, but may contribute to the efficacy of the active agent.

Uses

In embodiments, relacorilant is suitable for use in the treatment of disorders characterized by cortisol excess. For example, in embodiments, pharmaceutical formulations containing relacorilant are suitable for use in the treatment of Cushing's syndrome, including Cushing's Disease, and other diseases and disorders. Such treatments may be administered alone, or in combination with other treatments for such diseases and disorders.

The pharmaceutical formulations containing relacorilant and the methods disclosed herein comprising administration of pharmaceutical formulations containing relacorilant may be useful in treating patients suffering from any condition amenable to treatment with a GRM. Conditions amenable to treatment with a GRM may include without limitation, for example, obesity, diabetes, hyperglycemia, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, and migraine headaches. In some embodiments, the disorder or condition can be major psychotic depression, a stress disorder or antipsychotic induced weight gain. In embodiments, the disorder or condition can be selected from obesity, diabetes, hyperglycemia, hypertension, depression, anxiety, and Cushing's Syndrome. In embodiments, the disorder or condition can be Cushing's Syndrome, and may be, in particular embodiments, Cushing's Disease, and may include hyperglycemia secondary to hypercortisolism.

Other conditions that can be treated using the formulations disclosed herein include alcohol dependence, symptoms of alcohol withdrawal, and cognitive deficits associated with excess alcohol consumption. The formulations disclosed herein can also be used to treat cancer, such as cancer of the bone, breast, prostate, ovary, skin, brain, bladder, cervix, liver, lung, and other cancers, including, without limitation, leukemia, lymphoma, neuroblastoma, among others.

EXAMPLES

The following examples are presented by way of illustration of embodiments of the methods disclosed herein, and serve to illustrate, but not to limit, the present disclosure of formulations containing relacorilant.

In the following examples, excipients included: glycerides, e.g., Lauroyl polyoxyl glycerides, such as Lauroyl polyoxyl-32 glycerides and diglycerides; including propylene glycols, such as propylene glycol monocaprylate; sorbitol; glycerin; and including blends of sorbitol and glycerin; and may have included colorants and anti-oxidants such as, e.g. butylated hydroxytoluene (BHT). Purified water was also used as needed.

In further embodiments, formulations may include surfactants, including without limitation polysorbate (polyoxyethylene sorbitan monolaureate) surfactants and detergents (such as, e.g., Tween® 20, Tween® 80, and others); lipids, such as, e.g., corn oil, castor oil, cottonseed oil, olive oil, peanut oil, and other oils, including hydrogenated vegetable oils, medium-chain triglycerides of coconut oil and palm seed oil, and other oils suitable for use in pharmaceutical compositions for human administration; solubilizers (including solvents and solubility enhancers), such as, e.g., polyethylene glycols (PEG), ethanol, propylene glycol, glycerin, N-methyl-2-pyrrolidone, dimethylacetamide, dimethylsulfoxide, and other water-soluble organic solvents without limitation; and antioxidants such as BHT, butylated hydroxyanisole (BHA), tert-butyl hydroquinone (TBHQ), vitamin E (alpha tocopherol), and others without limitation.

In the following examples, the gel capsules used were softgel capsules, and included gelatin, sorbitol, and glycerin. In addition, the softgel capsules typically further included purified water (as needed for gel preparation), and colorants if desired. An exemplary gel capsule shell included 195.05 g gelatin; and 111.46 g of a sorbitol-glycerin blend containing equal amounts of sorbitol and glycerin, with smaller amounts of D-glucitol. The sorbitol-glycerin blend is commercially available as "Sorbitol Special™ from SPI Pharma (Septemes, FR).

As noted above, many GRMs, including many HKFA GRMs such as relacorilant, are poorly soluble in pharmaceutically acceptable compositions and solvents; in addition, pharmaceutical formulations of many such GRMs, including many such HKFA GRMs, often provide only poor bioavailability. In addition, many GRMs, including many HKFA GRMs, are difficult to formulate so as to provide acceptable stability. Many GRMs, such as relacorilant, are not stable over time in some formulations, particularly in basic (low pH) formulations, or when exposed to light, or under other storage conditions. Due to the requirements for solubilization, and the solvents needed for such solubilization, many GRMs, including many HKFA GRMs, are difficult to formulate so as to provide acceptable biocompatibility of the pharmaceutical formulation (e.g., to provide formulations which do not include, or only include minimal amounts of, excipients which may have uncomfortable, adverse, or toxic effects on the subject to which they are administered).

The following examples discuss several exemplary relacorilant-containing formulations prepared as discussed herein. All of the formulations discussed herein are believed to provide useful amounts of solubilization of the active ingredient, and to provide sufficient formulation stability, including sufficient stability of the active ingredient, so as to be suitable for use in the administration of pharmaceutically active compounds to human subjects. Suitable stability includes the ability of a formulation to maintain effective amounts of relacorilant over time (over a period of months, or potentially even years, of storage). In particular, all of the formulations discussed herein are believed to provide useful amounts of solubilization of relacorilant, and to provide sufficient formulation stability, including sufficient stability of the relacorilant, so as to be suitable for use in the administration of relacorilant to human subjects. In addition, the formulations disclosed herein are believed to provide improved bioavailability of relacorilant as compared to prior or alternative formulations. The formulations including relacorilant disclosed herein are further believed to provide improved biocompatibility as compared to prior or alternative formulations. The formulations disclosed herein, being suitable for use in the administration of relacorilant to human subjects, are believed to be suitable for use in the treatment of human subjects suffering from disorders amenable to treatment by HKFA compounds such as relacorilant. The formulations disclosed herein are believed to provide improved pharmaceutical formulations which solve the problems of poor solubility, or poor bioavailability, or poor biocompatibility, or poor stability, previously encountered with prior or alternative formulations of relacorilant for administration to human subjects.

The following examples are provided by way of illustration only and not by way of limitation. Those of skill will readily recognize a variety of noncritical parameters which could be changed or modified to yield essentially similar results.

Example 1 "Clinical Formulation"

Relacorilant was found to be stable in acidic aqueous solutions; however, relacorilant was found to degrade over time in neutral solutions at elevated temperatures, and was found to be sensitive to basic conditions. Relacorilant stability and compatibility with various excipients was tested and suitable excipients were identified. An initial formulation comprising a polyethoxylated castor oil (Kolliphor EL, available from BASF, Florham Park, New Jersey) and a monodiglyceride mixture (Capmul MCM, a monodiglyceride of medium chain, mainly caprylic and capric, fatty acids, available from ABITEC Corporation, Columbus, Ohio) demonstrated significant decomposition (i.e., instability) when stability was tested for two weeks at 40° C. at 75% relative humidity, and at 60° C. Other formulations including propylene glycol monocaprylates (Capryol PGMC, available from Gattefosse USA, New Jersey) and stearoyl polyoxyl-32 glycerides (Gelucire 50/13, available from Gattefosse USA, New Jersey) failed to provide desirable dissolution properties. Lauryl polyoxyl-32 glycerides (Gelucire 44/14, available from Gattefosse USA, New Jersey) in place of the stearoyl polyoxyl-32 glycerides were then used. As discussed below, the formulation of Table III surprisingly provided improved stability, suitable for use in relacorilant formulations for administration to human patients, including oral administration.

Several test formulations were prepared and subjected to stability and other testing. The compositions of these test formulations are presented in Table I, in which "API" is relacorilant; "MDC" indicates medium-chain monodiglycerides (mainly caprylic and capric); "PEC" indicates polyethoxylated castor oil; "LPG" indicates lauroyl polyoxyl-32 glycerides; "PGM" indicates propylene glycol monocaprylates; "BHT" indicates butylated hydroxytoluene; "BHA" indicates butylated hydroxyanisole; "GLT" indicates propyl gallate; "MYR" indicates myristic acid; and "AT" indicates α-Tocopheral.

TABLE I

TEST FORMULATIONS

| Formulation | Composition (weight %) | pH |
|---|---|---|
| A | 20 API, 40 MDC, 40 PEC | 7.0 |
| B | 20 API, 39.96 MDC, 40 PEC, 0.04 BHT | |
| C | 20 API, 39.91 MDC, 40 PEC, 0.04 BHT, 0.04 BHA | |
| D | 20 API, 39.76 MDC, 40 PEC, 0.04 BHT, 0.2 GLT | 7.0 |
| E | 20 API, 39.8 MDC, 40 PEC, 0.2 AT | |

TABLE I-continued

TEST FORMULATIONS

| Formulation | Composition (weight %) | pH |
|---|---|---|
| F | 20 API, 39.26 MDC, 40 PEC, 0.04 BHT, 0.2 GLT, 0.5 MYR | |
| G | 20 API, 59.98 LPG, 20 PGM, 0.02 BHT | 4.0 |

The stability of relacorilant in the several test formulations was examined for two weeks at 50° C. The degree of degradation seen with the preferred formulation (formulation G in Table I above) was suggestive of a good compatibility with these reagents during manufacturing and long term storage. Amounts of relacorilant and relacorilant-derived impurities were measure by high pressure liquid chromatography (HPLC). There was no significant reduction in the amount of relacorilant in formulation G after two weeks storage at 50° C. The highest percentage of relacorilant, the least amount of impurities, and the smallest increase in impurities after two weeks storage at 50° C. was found with formulation G, as compared to the other formulations.

The stability of relacorilant in a series of potential excipients was also examined for two weeks at 40° C. at 75% relative humidity, and at 60° C., including in formulations of Table I. The predominant degradation path was through formation of the aromatic decarbonylation of relacorilant with both propylene glycol monocaprylate and lauroyl polyoxyl-32 glyceride excipients. Relacorilant stability was good with both these excipients. In the formulation of Table I, relacorilant showed good stability at 40° C./75% RH. Degradation was more pronounced in lauroyl polyoxyl-32 glycerides than propylene glycol monocaprylates at 60° C.; however, the degree of degradation seen was suggestive of a good compatibility with these reagents during manufacturing and long term storage. These results are presented in Table II (showing purity, as measured by % of (relacorilant at the end of the test period) compared to (the total of relacorilant plus relacorilant-derived impurities).

TABLE II

Compatibility of Relacorilant with Excipients

| | | | 40° C./75% RH | | 60° C. | |
|---|---|---|---|---|---|---|
| Ingredient | Control | T₀ | T (1 week) | T (2 week) | T (1 week) | T (2 week) |
| Propylene glycol monocaprylate | 98.03% | 98.09% | 98.00% | 97.84% | 97.51% | 96.65% |
| Lauroyl polyoxyl-32 Glycerides | 98.09% | 98.13% | 97.64% | 97.55% | 97.22% | 96.77% |

As a result of such testing, the final, improved formulation was determined.

The following Table III provides an improved formulation suitable for incorporation of relacorilant in a softgel capsule with improved dissolution and stability. The formulation may be used to provide, e.g., 100 mg relacorilant per capsule (which may be suitable, for example, for administration to patients suffering from Cushing's syndrome or Cushing's Disease). The formulation may also be used to provide 150 mg relacorilant per capsule, or other amounts of relacorilant, with appropriately scaled percentages of other ingredients (retaining the same relative proportions of all ingredients).

The formulation of Table III included the following ingredients (percentages are weight percent):

TABLE III

"Clinical Formulation"

| Ingredients | Function | Composition (% w/w) | Per 100 mg Relacorilant Dosage Form |
|---|---|---|---|
| Relacorilant | API | 20.0 | 100 mg |
| Lauryl polyoxyl-32 glycerides | Surfactant | 59.98 | 299.9 mg |
| propylene glycol monocaprylates | Solubilizer | 20.0 | 100 mg |
| BHT, BHA | Antioxidant | 0.02 | 0.1 mg |
| Total | | 100% | 500 mg |

Relacorilant (the API) solubilizes well in this formulation, and is stable in this formulation. This formulation is semi-solid. The formulation provides suitable bioavailability for clinical use, as shown in the pharmacokinetic profile illustrated in FIG. 1. Eight fasted human volunteers were administered 150 milligrams of relacorilant in the formulation of Table III, and the plasma levels of relacorilant were measured over time after administration. Mean (with standard deviations) of the eight subjects are shown. Peak plasma concentrations of about 175 ng/mL were measured in these subjects.

This formulation was tested for stability. Stability testing included testing of some formulations for up to one year. Applicant has determined that relacorilant is sensitive to both moisture and light. In addition, Applicant has determined that relacorilant is more stable in formulations having neutral or acidic pH, while it is significantly less stable over time in formulations having basic pH (e.g., particularly at pH greater than 8).

Figure 2:
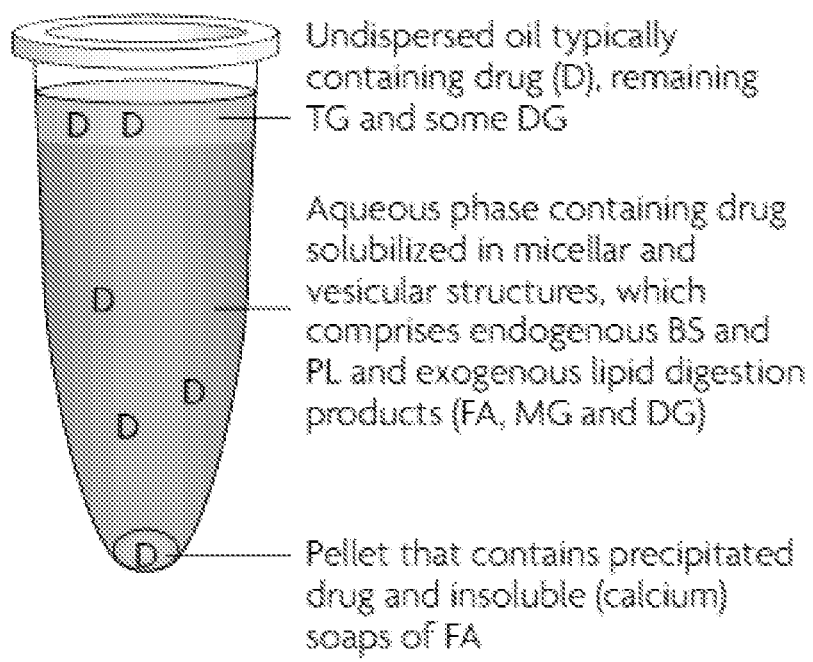
FIG. 2 illustrates an idealized side view of a container used for in vitro digestion testing of test formulations. The container holds three phases into which the active pharmaceutical ingredient may partition.

An in vitro model was also used to model the effects of digestion of the formulation (see Williams H D et al., *J. Pharm Sci.* 101:3360-3380 (2012)). A schematic diagram illustrating the in vitro model is shown in FIG. 2. The results of this testing is believed to be indicative of the bioavailability of the drug product when administered in vivo. The in vitro digestive model includes three phases in a single container: i) a pellet that contains precipitated drug and insoluble (e.g., calcium) soaps of fatty acids; ii) an aqueous phase containing drug solubilized in micellar and vesicular structure, which comprises bile salts (BS, such as, e.g., sodium taurodeoxycholate as used by Williams et al.) and phospholipids (PL) and exogenous lipid digestion products (e.g., fatty acids (FA), monoglycerides (MG), and diglycerides (DG)); and iii) an undispersed oil phase, typically containing drug, remaining triglycerides (TG), and some diglycerides (DG). The experimental configuration used when performing an in vitro digestion model is shown in FIG. 2, which illustrates an idealized side view of a container used for in vitro digestion testing of test formulations. The container holds three phases into which the active pharmaceutical ingredient may partition. The amount of API which is found in each of the three phases provides a measure of the expected behavior of the API in vivo, and allows comparison of the expected bioavailability that would result from the formulations being compared. For example, the amount of API found in the aqueous phase provides an estimate of the amount (or proportion) of the API that would be found in the plasma of a subject following administration of the API in that formulation.

Figure 3:
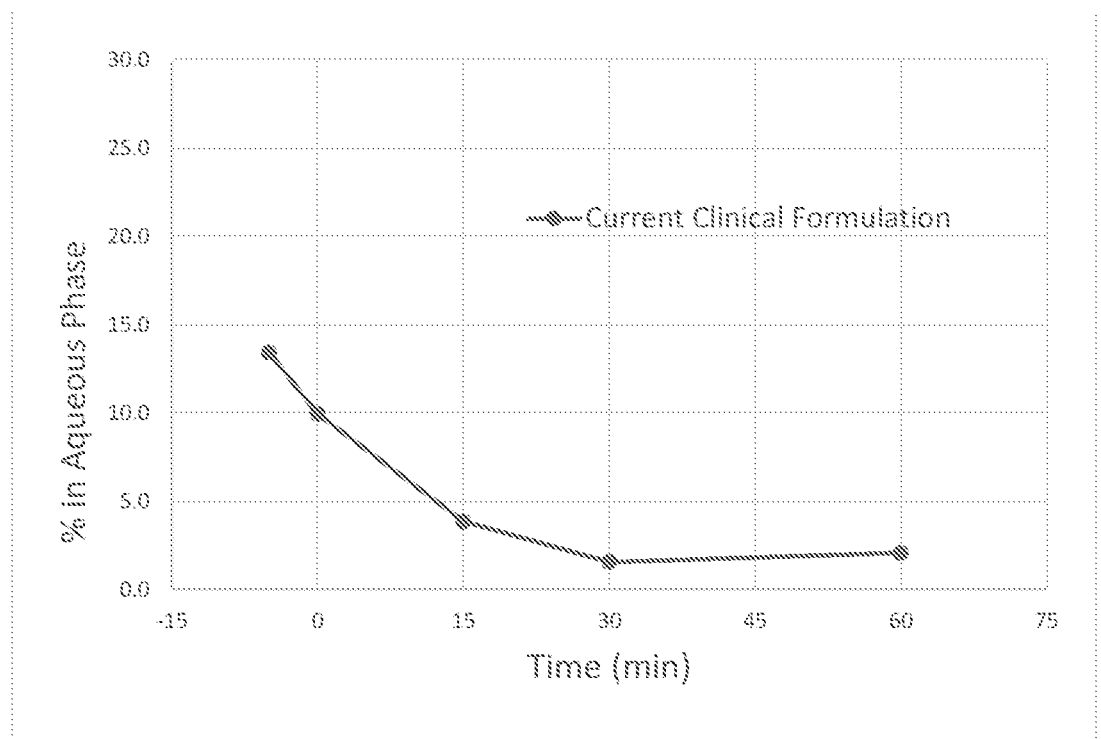
FIG. 3 shows the results of in vitro digestion testing per FIG. 2, indicating that up to about 15% of the formulation of Table I partitioned into the aqueous phase during the early phases of the in vitro testing, and about 10% partitioned into the aqueous phase at time zero of the testing.

FIG. 3 shows the results of in vitro digestion testing for the formulation of Table III. The data presented in FIG. 3 illustrate the performance of the formulation of Table III in the in vitro digestion model over time. Approximately 10-15% percent of relacorilant partitioned into the aqueous phase early on during the testing, and then that percentage was reduced over time. These results further indicate that there is a correlation between in vitro digestion model and human PK profile for the formulation (see FIG. 1).

The formulation of Table III was also administered to monkeys for in vivo testing (100 mg of the API, relacorilant). These results show considerable plasma exposure ($AUC_{inf}$) in monkeys. These results are presented in Table IV.

TABLE IV 100 mg Dose

| Parameter | Plasma Levels (Clinical Formulation) |
|---|---|
| $C_{max}$ (ng/mL) | 1266 |
| $AUC_{inf}$ | 11653 |
| $AUC_{0-24}$ | 10347 |

In embodiments, it will be understood by those of skill in the art that modifications to these formulations may include: using purified commercial excipients (for example, purified Kolliphor ELP significantly reduces impurities as compared to Kolliphor products not labeled as "purified"); and lower pH (e.g., pH of less than pH 8, and preferably about pH 7 or less) may help to further reduce impurities. It is believed that reducing impurities improves the stability and other performance parameters of the formulation.

Other relacorilant-containing formulation have been prepared, some prior to the preparation of Table III, some prepared after its testing in attempts to improve on the formulation of Table III. For example, an initial formulation comprising a polyethoxylated castor oil with a monodiglyceride mixture (a monodiglyceride of medium chain, mainly caprylic and capric, fatty acids) demonstrated significant decomposition (i.e., instability) when stability was tested for two weeks at at 40° C. at 75% relative humidity, and at 60° C. An attempt to improve the formulation of Table III (a formulation of 20% relacorilant, 40% polyoxylated castor oil surfactant, and 40% glycerol caprylate solubilizer, where percent is weight percent) was found to be unstable (impurities increased 4.5% in one month at 40° C. at 75% relative humidity), and proved to be unsuitable for clinical use for at least that reason. Accordingly, the formulation of Table III was found to be surprisingly stable while providing suitable bioavailability, in contrast to all other formulations tested. Thus, the formulation of Table III provides surprising and unexpected advantages over other formulations.

Example 2 Formulations for a Range of Relacorilant Amounts

Relacorilant formulations may be provided which include multiple amounts of relacorilant. For example, single unit dosage forms each containing 25 mg, 50 mg, 100 mg, 200 mg, 300 mg, 400 mg, and 500 mg of relacorilant may be prepared according to the methods provided herein. This example provides instructions for preparing relacorilant formulations for the preparation of formulations for use in single unit dosage forms of relacorilant containing a range of relacorilant amounts. The single unit dosage forms may be softgel capsules containing these formulations.

TABLE V

Relacorilant Formulations (for Several Dose Amounts)

| Component | Amount per capsule (mg) Capsule Fill Formulation: | | | | | | |
|---|---|---|---|---|---|---|---|
| Relacorilant | 25.00 | 50.00 | 100.00 | 200.00 | 300.00 | 400.00 | 500.00 |
| Lauroyl polyoxyl-32 glycerides | 74.975 | 149.95 | 299.90 | 599.80 | 899.70 | 1199.60 | 1499.50 |
| Propylene glycol monocaprylate | 25.00 | 50.00 | 100.00 | 200.00 | 300.00 | 400.00 | 500.00 |
| Butylated hydroxytoluene (BHT) | 0.025 | 0.05 | 0.10 | 0.20 | 0.30 | 0.40 | 0.50 |
| Total Weight | 125 | 250 | 500 | 1000 | 1500 | 2000 | 2500 |

Softgel capsules may be filled with the formulations described in Table V above to provide single unit dosage forms containing the desired amounts of relacorilant. Softgel capsules containing the relacorilant formulations described in Table V may be made of about 50% to about 75% gelatin and about 25% to about 50% of a sorbitol/glycerin blend (by weight), with purified water and/or colorants included as needed. In some embodiments, softgel capsules containing these relacorilant formulations may be made of about 60% to about 70% gelatin and about 30% to about 40% of a plasticizer, or about 63% to about 66% gelatin and about 34% to about 37% of a plasticizer, with purified water and/or colorants included as needed. In particular embodiments, softgel capsules containing these relacorilant formulations may be made of 64% gelatin and 36% of a sorbitol/glycerin blend (by weight), or of 63.64% gelatin and 36.36% of a sorbitol/glycerin blend (by weight), these percentages not including the weight of any purified water and/or colorants that may be included as needed.

All patents, patent publications, publications, and patent applications cited in this specification are hereby incorporated by reference herein in their entireties as if each individual publication or patent application were specifically and individually indicated to be incorporated by reference. In addition, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A formulation for oral administration of relacorilant, (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone, which has the following structure:

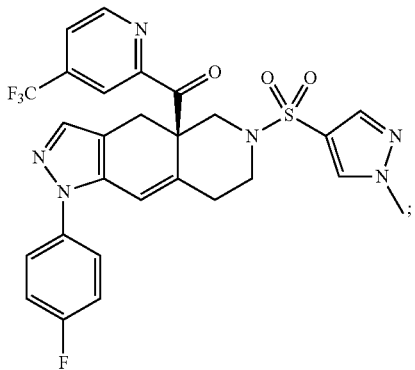

the formulation comprising:
about 18 to 22% relacorilant;
about 56% to 64% surfactant, wherein said surfactant is lauroyl polyoxyl glyceride, and
about 18% to 22% solubilizer, wherein said solubilizer is propylene glycol monocaprylate,
wherein said percentages are weight percent.

2. The formulation of claim 1, further including the antioxidant selected from butylated hydroxytoluene (BHT).

3. The formulation of claim 2, wherein the formulation comprises about 0.02% antioxidant by weight of the formulation.

4. The formulation of claim 2, consisting of 20% relacorilant, 59.98% surfactant, 20% solubilizer, and 0.02% antioxidant.

5. The formulation of claim 4, consisting of 25 mg relacorilant, 74.975 mg surfactant, 25 mg solubilizer, and 0.025 mg antioxidant.

6. The formulation of claim 4, consisting of 50 mg relacorilant, 149.95 mg surfactant, 50 mg solubilizer, and 0.05 mg antioxidant.

7. The formulation of claim 4, consisting of 100 mg relacorilant, 299.9 mg surfactant, 100 mg solubilizer, and 0.1 mg antioxidant.

8. The formulation of claim 4, consisting of 150 mg relacorilant, 349.85 mg surfactant, 150 mg solubilizer, and 0.15 mg antioxidant.

9. The formulation of claim 4, consisting of 200 mg relacorilant, 599.8 mg surfactant, 200 mg solubilizer, and 0.2 mg antioxidant.

10. The formulation of claim 4, consisting of 300 mg relacorilant, 899.7 mg surfactant, 300 mg solubilizer, and 0.3 mg antioxidant.

11. The formulation of claim 4, consisting of 400 mg relacorilant, 1199.6 mg surfactant, 400 mg solubilizer, and 0.4 mg antioxidant.

12. The formulation of claim 4, consisting of 500 mg relacorilant, 1499.5 mg surfactant, 500 mg solubilizer, and 0.5 mg antioxidant.

13. consisting essentially of a softgel capsule containing a relacorilant formulation consisting of 20% relacorilant, 59.98% surfactant, wherein said surfactant is lauroyl polyoxyl glyceride, and 20% solubilizer, wherein said solubilizer is propylene glycol monocaprylate, and 0.02% antioxidant, wherein said antioxidant is butylated hydroxytoluene (BHT), wherein said percentages are weight percentages.

14. The unit dose for oral administration of relacorilant of claim 13, said softgel capsule containing a relacorilant formulation consisting of 25 mg relacorilant, 74.975 mg surfactant, 25 mg solubilizer, and 0.025 mg antioxidant.

15. The unit dose for oral administration of relacorilant of claim 13, said softgel capsule containing a relacorilant formulation consisting of 50 mg relacorilant, 149.95 mg surfactant, 50 mg solubilizer, and 0.05 mg antioxidant.

16. The unit dose for oral administration of relacorilant of claim 13, said softgel capsule containing a relacorilant formulation consisting of 100 mg relacorilant, 299.9 mg surfactant, 100 mg solubilizer, and 0.1 mg antioxidant.

17. The unit dose for oral administration of relacorilant of claim 13, said softgel capsule containing a relacorilant formulation consisting of 150 mg relacorilant, 349.85 mg surfactant, 150 mg solubilizer, and 0.15 mg antioxidant.

18. The unit dose for oral administration of relacorilant of claim 13, said softgel capsule containing a relacorilant formulation consisting of 200 mg relacorilant, 599.8 mg surfactant, 200 mg solubilizer, and 0.2 mg antioxidant.

19. The unit dose for oral administration of relacorilant of claim 13, said softgel capsule containing a relacorilant formulation consisting of 300 mg relacorilant, 899.7 mg surfactant, 300 mg solubilizer, and 0.3 mg antioxidant.

20. The unit dose for oral administration of relacorilant of claim 13, said softgel capsule containing a relacorilant formulation consisting of 400 mg relacorilant, 1199.6 mg surfactant, 400 mg solubilizer, and 0.4 mg antioxidant.

21. The unit dose for oral administration of relacorilant of claim 13, said softgel capsule containing a relacorilant formulation consisting of 500 mg relacorilant, 1499.5 mg surfactant, 500 mg solubilizer, and 0.5 mg antioxidant.

* * * * *

UNITED STATES PATENT AND TRADEMARK OFFICE
CERTIFICATE OF CORRECTION

| | |
|---|---|
| PATENT NO. | : 11,925,626 B2 |
| APPLICATION NO. | : 17/950902 |
| DATED | : March 12, 2024 |
| INVENTOR(S) | : Ian Scott, Travis Lemons and Yip-Fong Chia |

It is certified that error appears in the above-identified patent and that said Letters Patent is hereby corrected as shown below:

In the Claims

Column 27, Line 37, Claim 2: delete "selected from".

Column 28, Line 13, Claim 13: insert --A unit dose for oral administration of relacorilant-- before the word "consisting".

Signed and Sealed this
Twenty-third Day of April, 2024

Katherine Kelly Vidal
*Director of the United States Patent and Trademark Office*